United States Patent
Han et al.

(10) Patent No.: US 9,169,206 B2
(45) Date of Patent: Oct. 27, 2015

(54) ORGANIC SEMICONDUCTOR COMPOUND, METHOD FOR PREPARING THE SAME, AND ORGANIC SEMICONDUCTOR COMPOSITION, AND ORGANIC SEMICONDUCTOR THIN FILM AND ELEMENT CONTAINING THE SAME

(75) Inventors: Sung Hwan Han, Seoul (KR); Cheon Gyu Cho, Seoul (KR)

(73) Assignee: Luminano Co., Ltd., Seoul (KR)

( * ) Notice: Subject to any disclaimer, the term of this patent is extended or adjusted under 35 U.S.C. 154(b) by 224 days.

(21) Appl. No.: 13/141,135

(22) PCT Filed: Dec. 23, 2009

(86) PCT No.: PCT/KR2009/007749
§ 371 (c)(1),
(2), (4) Date: Jun. 21, 2011

(87) PCT Pub. No.: WO2010/074520
PCT Pub. Date: Jul. 1, 2010

(65) Prior Publication Data
US 2011/0253944 A1    Oct. 20, 2011

(30) Foreign Application Priority Data
Dec. 23, 2008    (KR) ........................ 10-2008-0132675

(51) Int. Cl.
| C09B 5/00 | (2006.01) |
| C07D 209/02 | (2006.01) |
| C07D 209/04 | (2006.01) |
| C07D 209/08 | (2006.01) |
| C07D 209/26 | (2006.01) |
| C07D 209/86 | (2006.01) |
| C07D 209/88 | (2006.01) |
| C07D 471/22 | (2006.01) |
| C07D 487/04 | (2006.01) |
| C07D 487/14 | (2006.01) |
| H01L 51/00 | (2006.01) |

(52) U.S. Cl.
CPC ............ *C07D 209/02* (2013.01); *C07D 209/04* (2013.01); *C07D 209/08* (2013.01); *C07D 209/26* (2013.01); *C07D 209/86* (2013.01); *C07D 209/88* (2013.01); *C07D 471/22* (2013.01); *C07D 487/04* (2013.01); *C07D 487/14* (2013.01); *H01L 51/0072* (2013.01); *Y02E 10/549* (2013.01)

(58) Field of Classification Search
CPC ..... C07D 409/14; C07D 495/22; H01L 29/08
USPC .......... 252/500; 548/416, 417, 469, 500, 441, 548/443; 546/36; 549/41
See application file for complete search history.

(56) References Cited

U.S. PATENT DOCUMENTS

| 2008/0142792 A1* | 6/2008 | Park et al. ........................ 257/40 |
| 2009/0043113 A1* | 2/2009 | Park et al. ........................ 549/41 |

FOREIGN PATENT DOCUMENTS

| CN | 101200471 A | 6/2008 |
| JP | 2004-123619 A | 4/2004 |
| JP | 2007-227907 A | 9/2007 |
| JP | 2010-059147 A | 3/2010 |
| WO | 2007/140847 A1 | 12/2007 |

OTHER PUBLICATIONS

Wu et al., Indolo[3,2-b]carbazole-Based Thin-Film Transistors with High Mobility and Stability, 2004, J. Am. Chem. Soc. 127, 614-618.*
Bocchi et al., Tetrahedron vol. 42, No. 18. pp. 5019-5024, 1986.*
Samsoniya, et al., "New Synthesis of 1H, 5H-Pyrrolo [2,3-f] Indole and 3H, 6H-Pyrrolo [3,2-e] Idole", Chemistry of heterocyclic compounds, the fourth issue, vol. 18, Apr. 21, 1982, p. 382-385.
Icli, et al., "Fluoresence Quenching Between Strong π-electron Donor-acceptors of Carbazolocarbazole and Tetranitrofluorenone Leading to Electron Transfer", Journal of Luminescence, vol. 75, Jun. 16, 1997, p. 353-359.
Pindur, et al., "First Synthesis of 2-Vinylindole and its Diels-Alder Reactions with CC-Dienophiles", Helvetica Chimica Acta, the fifth issue, vol. 71, Dec. 31, 1988, pp. 1060-1064.
Fukuda, et al., "Novel Seco Cyclopropa[c]pyrrolo[3,2-e]indole Bisalkylators Bearing a 3,3'-Arylenebisacryloyl Group as a Linker", J. Med. Chem., the ninth issue, vol. 44, Oct. 11, 2001, pp. 1396-1406.
Song, et al., Electrochemical Method for Determination of the Energy Band Structure of Carbazole Derivatives, Journal of Luminescence, vol. 26, No. 1, Feb. 28, 2005.
Avijit Banerji, et al., "A New Route to the Synthesis of Indolo[2,3-a]carbazoles", Chemistry Letter, the eleventh issue, vol. 34, pp. 1500-1501, 2005.
Hervé Royer, et al., "Synthesis of Pentacyclic Heteroaromatic Systems Related to Indolocarbazoles Alkaloids", Synthetic Communications, the seventh issue, vol. 28, pp. 1239-1251.
Yong-Zhou Hu, et al., "An Efficient and General Synthesis of Indolo[2,3-a]carbazoles Using the Fischer Indole Synthesis", Synlett, vol. 1, pp. 42-48, Nov. 29, 2004.

(Continued)

*Primary Examiner* — Monique Peets
(74) *Attorney, Agent, or Firm* — Greer Burns & Crain Ltd.

(57) ABSTRACT

The present invention relates to a novel polycyclic aromatic organic semiconductor compound having a polycyclic aromatic core, a method for preparing the same, and electronic, optical or electro-optical devices such as an organic semiconductor composition, organic semiconductor thin film, organic field effect transistor and solar cell containing the compound. The novel organic semiconductor compound according to the present invention has high crystallinity and control capability, and facilitates control of doping conditions in the manufacture of organic semiconductor element so that it can be used for diverse applications. The compound can be mass-produced at low cost and has high solubility in organic solvents so that a liquid phase process can be applied to the manufacture of semiconductor elements and the like, thus enabling the mass-production of semiconductor elements and solar cells at low cost.

14 Claims, No Drawings

(56) References Cited

OTHER PUBLICATIONS

Larisa N. Yudina, et al., "Synthesis and alkylation of indolo[3,2-b]carbazoles", Tetrahedron, vol. 59, pp. 1265-1275, Feb. 17, 2003.

Hans-Joachim Knolker, et al., "Transition Metal Complexes in Organic Synthesis—44.1 Iron-mediated Synthesis of Indolo[2,3-b]carbazole", Tetrahedron Letters, vol. 39, pp. 4007-4008.

Paola Manini, et al., "Acid-Promoted Competing Pathways in the Oxidative Polymerization of 5,6-Dihydroxyindoles and Related Compounds: Straightforward Cyclotrimerization Routes to Diindolocarbazole Derivatives", J.Org.Chem, the twentieth issue, vol. 63, pp. 7002-7008, Sep. 12, 1998.

Quan Zhang, et al., "Synthesis of 6H-Indolo[2,3-b][1,6]naphthyridines and Related Compounds as the 5-Aza Analogues of Ellipticine Alkaloids", J. Org. Chem, the twenty-third issue, vol. 65, pp. 7977-7983, Oct. 21, 2000.

Vittorio Bocchi, et al., "Synthesis and Characterization of New Indole Trimers and Tetramers", Tetrahedron, vol. 42, No. 18, pp. 5019-5024, Dec. 31, 1986.

* cited by examiner

ORGANIC SEMICONDUCTOR COMPOUND, METHOD FOR PREPARING THE SAME, AND ORGANIC SEMICONDUCTOR COMPOSITION, AND ORGANIC SEMICONDUCTOR THIN FILM AND ELEMENT CONTAINING THE SAME

TECHNICAL FIELD

The present invention relates to a novel polycyclic aromatic organic semiconductor compound having a polycyclic aromatic core, a method for preparing the same, and electronic, optical or electro-optical devices such as an organic semiconductor composition, organic semiconductor thin film, organic field effect transistor and solar cell containing the compound.

BACKGROUND ART

The introduction of an organic semiconductor makes it possible to realize a flexible display that can be manufactured on a flexible plastic substrate. Since a result of research showing that polyacetylene as a simple conjugate polymer has semiconductor properties and if polyacetylene is doped, it may have electrical conductivity of metal was reported, research and development on organic semiconductor materials, especially organic light emitting diodes, has been in progress and various mobile electronic devices employing organic light emitting diodes have been commonly used. Further, it has been tried to manufacture a driving mechanism for such organic light emitting diodes with organic materials, and, thus, technology development on organic thin film transistors has been in progress.

A configuration and a principle of operation of the organic thin film transistors are basically the same as those of metal oxide semiconductor field effect transistors (MOSFET) using amorphous silicon or polycrystalline silicon. However, the biggest difference between the organic thin film transistor and the MOSFET is using an organic semiconductor as a semiconductor material instead of using silicon. Even a few years ago, an organic thin film transistor using an organic semiconductor as an active layer semiconductor material, a glass substrate or a silicon wafer, having very low, electrical resistance as a substrate, and metal and an inorganic oxide film as an electrode and an insulating layer, respectively, has been researched. However, recently, research on an organic thin film transistor (TFT) using polymer materials for a substrate, an insulating layer and an electrode has been in progress, and, thus, a public use of a flexible display has been accelerated.

In addition to this, development of an organic semiconductor is important in developing organic solar cells. Solar cells mainly feature p-n junction solar cells using silicon, but improvement in a performance and price competitiveness of the solar cells may reach the limit. Therefore, development of new solar cells which can overcome limitations of conventional solar cells is needed. There have been suggested various solar cells over silicon solar cells, and an organic solar cell capable of remarkably improving an economic feasibility of a silicon solar cell has been regarded as having greatest potential. The most important thing in developing organic solar cells is development of a light absorbing layer that absorbs lights and development of an n-type semiconductor layer and a p-type semiconductor layer that receive electron holes and electrons generated when the light absorbing layer absorbs lights. Various organic polymer have been developed as a p-type semiconductor, and, thus, it is possible to make a selection in various ways, but there has not been suggested a particular system having a distinctively excellence as an n-type semiconductor. In a dye-sensitized solar cell, $TiO_2$ has been used to form an n-type semiconductor and a light sensitizer using ruthenium organic metal compound has been used. However, such a technology has been technically protected and is expensive. Eventually, the development of the organic semiconductor is most important in developing organic solar cells having high efficiency and price competitiveness.

It is possible to reduce manufacturing cost with a semiconductor device and a solar cell using an organic semiconductor as compared with a conventional semiconductor device using an inorganic semiconductor such as Si, and the semiconductor device and solar cell using the organic semiconductor have been expected to have flexibility. Various organic semiconductor compositions such as polythiophene and rubrene have been researched, and it has been reported that a transistor including a channel forming area formed of such organic semiconductor compositions has mobility equal to or similar to mobility of a transistor including a channel forming area formed of amorphous silicon (see, for example, APL Vol. 80, No. 6, 1088-1090 (2002)).

A number of organic semiconductor compositions such as pentacene or conductive polymers having high mobility of electron holes have been known as p-type organic semiconductors used for organic TFTs, organic light emitting diodes, solar cells and the like.

However, if a channel forming area is formed of these organic semiconductor compositions, the organic semiconductor compositions are very slightly soluble in organic solvents and it is difficult to apply a coating process to these compositions, and, thus, a film is formed by vacuum deposition. These organic semiconductor compositions may have affinity with organic solvents by introducing alkyl chains or other substituents, so that these organic semiconductor compositions can be dissolved in the organic solvents. To be specific, it has been reported that poly-3-hexylthiophene (P3HT) formed by introducing a hexyl group to polythiophene is dissolved in organic solvents such as chloroform or toluene and a channel forming area is formed through a coating process such as a spin coating process (see, for example, APL 69(26) 4108-4100 (1996)).

Meanwhile, a polyacene compound as a condensed polycyclic compound is a molecule having a n-electron conjugated system in the same manner as polyacetylene or polyphenylene, and theoretically, the polyacene compound has a small band gap and has been expected to serve as an organic semiconductor composition having outstanding functions as compared with polyacetylene. A substituent introduced to the polyacene compound can be used for molecular binding or binding with a functional group of an insulating film surface and can be used to control a distance, a position and arrangement of an acene structure or can be used for patterning. The polyacene compound has benzene rings linearly connected to each other, and the polyacene compound which does not contain a substituent has a property of being slightly soluble in organic solvents as the number of benzene rings increases. Particularly, a polyacene compound having five or more linearly-fused benzene rings, such as pentacene, is not dissolved in most organic solvents and it is very difficult to form a uniform film through a spin coating process, and even if possible, an organic solvent and a temperature are very limited (for example, trichlorobenzene, 60° C.-180° C.).

Further, it has been widely known that as the number of benzene rings increases, the polyacene compound has low stability and particularly, pentacene has low resistance to oxidation and can be oxidized by oxygen in the air. As an example of introducing a substituent to a polyacene compound, 2,3,9,10-tetramethyl pentacene has been reported (see Wudl and Bao, Adv. Mater. Vol. 15, No. 3(1090-1093), 2003). However, 2,3,9,10-tetramethyl pentacene can be slightly dissolved in slightly heated o-dichlorobenzene and in reality, a channel forming area constituting a field effect transistor is formed by vacuum deposition.

It is also described in Japanese Patent Laid-open Publication No. 2004-256532 that 2,3,9,10-tetramethyl pentacene or 2,3-dimethyl pentacene is dissolved in o-dichlorobenzene. However, they are dissolved at temperature of 120° C. and it is not described that they can be dissolved at room temperature.

That is, a polyacene organic semiconductor compound such as pentacene needs a high production cost and can be sublimated under a depressurized atmosphere at 300° C. and decomposed in the air at a temperature higher than 300° C., and also, the polyacene organic semiconductor compound has low solubility to aqueous solvents and organic solvents, so that it is difficult to apply a liquid phase process to the polyacene organic semiconductor compound and instead, a gas phase process is applied to the polyacene organic semiconductor compound. Accordingly, a new organic semiconductor compound capable of solving the above-described problems has been demanded.

DISCLOSURE OF THE INVENTION

Problems to be Solved by the Invention

In view of the foregoing, the present invention provides a novel organic semiconductor compound capable of solving the above-described problems of a polyacene organic semiconductor compound such as pentacene. To be specific, the present invention provides a novel polycyclic aromatic organic semiconductor compound and a method for preparing the same. The novel organic semiconductor compound can be dissolved in organic solvents at a low temperature (for example, room temperature) and has high crystallinity and control capability and facilitates control of doping conditions in the preparation of organic semiconductor element, so that it can be used for diverse applications. Further, the novel polycyclic aromatic organic semiconductor compound can be mass-produced at low cost and has high solubility in organic solvents, so that a liquid phase process can be applied to the preparation of semiconductor elements and the like, thus enabling the mass-production of semiconductor elements at low cost. The present invention also provides an organic semiconductor composition, organic semiconductor thin film, and electronic, optical or electro-optical element containing the novel polycyclic aromatic organic semiconductor compound.

Means for Solving the Problems

In accordance with an aspect of the present invention, there is provided a polycyclic aromatic organic semiconductor compound represented by the following formula 1:

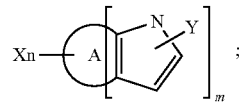
[Formula 1]

wherein in formula 1,

A is a ring selected from the group consisting of a substitutable 5-membered unsaturated or aromatic ring, a substitutable 6-membered unsaturated or aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group;

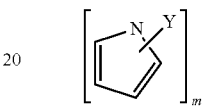

represents one or more pyrrol rings which may have a substituent Y, which is respectively fused with an end of A, and m is an integer of at least 1, Xn is a substituent independently selected from the following Substituent Group G1, which is bonded to A, and n is integer of 0 or at least 1:

<Substituent Group G1> the Substituent Group G1 consisting of a hydrogen, a halogen, a cyano group, a nitro group, a hydroxyl group, substituted or unsubstituted $C_1$-$C_{50}$ alkyl group, a substituted or unsubstituted $C_1$-$C_{50}$ alkoxy group, a substituted or unsubstituted $C_5$-$C_{50}$ cycloalkyl group, an substituted or unsubstituted $C_5$-$C_{50}$ heterocycloalkyl group, a substituted or unsubstituted $C_6$-$C_{50}$ aryl group, a substituted or unsubstituted $C_2$-$C_{50}$ heteroaryl group, an amine group, a carboxyl group, an acid anhydride, an ester group, a thiocarboxyl group, a dithiocarboxyl group, a sulfonic acid group, a sulfinic acid group, a sulfenic acid group, a sulfonyl group, a sulfinyl group, a haloacyl group, a carbamoyl group, a hydrazide group, an imide group, an amide group, an amidino group, an isocyano group, a cyanic ester group, an isocyanic ester group, a thiocyanic ester group, an isothiocyanic ester group, a formyl group, a thioformyl group, an acyl group, a thiol group, an amino group, an imino group, a hydrazino group, an alkoxy group, an aryloxy group, an ether group, a sulfide group, disulfide group, an silyl group, a germyl group, a stanyl group, a hosphino group and a boryl group; or Xn represents one or more rings respectively fused with an end of A, and n is an integer of 0 or at least 1, in which X is a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the group, in which each X may have one or more substituents selected from the Substituent Group G1; and Y is a substituent bonded to the pyrrol ring, being selected from the Substituent Group G1, or Y is a ring fused with the pyrrol ring, being a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group, in which Y may have one or more substituents selected from the Substituent Group G1.

In accordance with another aspect of the present invention, there is provided a method of preparing a novel polycyclic aromatic organic semiconductor compound in accordance with the present invention.

In accordance with still another aspect of the present invention, there is provided an organic semiconductor composition comprising one or more polycyclic aromatic organic semiconductor compounds in accordance with the present invention which are dissolved or dispersed in a solvent.

In accordance with still another aspect of the present invention, there is provided an organic semiconductor thin film comprising one or more polycyclic aromatic organic semiconductor compounds in accordance with the present invention.

In accordance with still another aspect of the present invention, there is provided an organic field effect transistor comprising one or more polycyclic aromatic organic semiconductor compounds in accordance with the present invention or an organic semiconductor thin film in accordance with the present invention.

In accordance with still another aspect of the present invention, there is provided an organic solar cell comprising one or more polycyclic aromatic organic semiconductor compounds in accordance with the present invention or an organic semiconductor thin film in accordance with the present invention.

In accordance with still another aspect of the present invention, there is provided an organic light emitting diode comprising one or more polycyclic aromatic organic semiconductor compounds in accordance with the present invention or an organic semiconductor thin film in accordance with the present invention.

In accordance with still another aspect of the present invention, there is provided a sensor comprising one or more polycyclic aromatic organic semiconductor compounds' in accordance with the present invention or an organic semiconductor thin film in accordance with the present invention.

In accordance with still another aspect of the present invention, there is provided an electronic, optical or electro-optical device comprising one or more polycyclic aromatic organic semiconductor compounds in accordance with the present invention or an organic semiconductor thin film in accordance with the present invention, which is selected from the group consisting of a thin film transistor (TFT), an integrated circuit component, a radio frequency identification (RFID) tag, an electronic light emitting display, a flat panel display, a backlight, a photodetector, a logic circuit, a memory device, a capacitor, a charge injecting layer, a Schottky diode, a planarising layer, an antistatic film, a conductive substrate or pattern, a photoconductor and an electrophotographic device.

Effect of the Invention

The present invention provides a novel polycyclic aromatic organic semiconductor compound and a method for preparing the same. The novel organic semiconductor compound can be dissolved in organic solvents at a low temperature (for example, room temperature) and has high crystallinity and control capability and facilitates control of doping conditions in the preparation of organic semiconductor element, so that it can be used for diverse applications. Further, the novel polycyclic aromatic organic semiconductor compound can be mass-produced at low cost and has high solubility in organic solvents, so that a liquid phase process can be applied to the preparation of semiconductor elements and the like, thus enabling the mass-production of semiconductor elements at low cost. The present invention also provides an organic semiconductor composition, organic semiconductor thin film, and electronic, optical or electro-optical element containing the novel polycyclic aromatic organic semiconductor compound. As the electronic, optical or electro-optical element containing the novel polycyclic aromatic organic semiconductor compound includes an organic field effect transistor (OFET), an organic light emitting diode (OLED), an organic solar cell, a sensor, a thin film transistor (TFT), an integrated circuit (IC) component, a radio frequency identification (RFID) tag, an electronic light emitting display, a flat panel display, a backlight, a photodetector, a logic circuit, a memory device, a capacitor, a PV cell, a charge injecting layer, a Schottky diode, a planarising layer, an antistatic film, a conductive substrate or pattern, a photoconductor or an electrophotographic device.

BEST MODE

In accordance with an aspect of the present invention, there is provided a polycyclic aromatic organic semiconductor compound represented by the following formula 1:

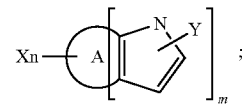

[Formula 1]

wherein in formula 1,

A is a ring selected from the group consisting of a substitutable 5-membered unsaturated or aromatic ring, a substitutable 6-membered unsaturated or aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group;

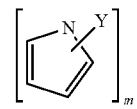

represents one or more pyrrol rings which may have a substituent Y, which is respectively fused with an end of A, and m is an integer of at least 1, Xn is a substituent independently selected from the following Substituent Group G1, which is bonded to A, and n is integer of 0 or at least 1:

<Substituent Group G1> the Substituent Group G1 consisting of a hydrogen, a halogen, a cyano group, a nitro group, a hydroxyl group, substituted or unsubstituted $C_1$-$C_{50}$ alkyl group, a substituted or unsubstituted $C_1$-$C_{50}$ alkoxy group, a substituted or unsubstituted $C_5$-$C_{50}$ cycloalkyl group, an substituted or unsubstituted $C_5$-$C_{50}$ heterocycloalkyl group, a substituted or unsubstituted $C_6$-$C_{50}$ aryl group, a substituted or unsubstituted $C_2$-$C_{50}$ heteroaryl group, an amine group, a carboxyl group, an acid anhydride, an ester group, a thiocarboxyl group, a dithiocarboxyl group, a sulfonic acid group, a sulfinic acid group, a sulfenic acid group, a sulfonyl group, a sulfinyl group, a haloacyl group, a carbamoyl group, a hydrazide group, an imide group, an amide group, an amidino group, an isocyano group, a cyanic ester group, an isocyanic ester group, a thiocyanic ester group, an isothiocyanic ester group, a formyl group, a thioformyl group, an acyl group, a thiol group, an amino group, an imino group, a hydrazino group, an alkoxy group, an aryloxy group, an ether group, a sulfide group, disulfide group, an silyl group, a germyl group, a stanyl group, a hosphino group and a boryl group; or Xn represents one or more rings respectively fused with an end of A, and n is an integer of 0 or at least 1, in which X is a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group, in which each X may have one or more substituents selected from the Substituent Group G1; and Y is a substituent bonded to the pyrrol ring, being selected from the Substituent Group G1, or Y is a ring fused with the pyrrol ring, being a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group, in which Y may have one or more substituents selected from the Substituent Group G1.

In accordance with another aspect of the present invention, there is provided a method of preparing a novel polycyclic aromatic organic semiconductor compound in accordance with the present invention.

In accordance with still another aspect of the present invention, there is provided an organic semiconductor composition comprising one or more polycyclic aromatic organic semiconductor compounds in accordance with the present invention which are dissolved or dispersed in a solvent.

In accordance with still another aspect of the present invention, there is provided an organic semiconductor thin film comprising one or more polycyclic aromatic organic semiconductor compounds in accordance with the present invention.

In accordance with still another aspect of the present invention, there is provided an organic field effect transistor comprising one or more polycyclic aromatic organic semiconductor compounds in accordance with the present invention or an organic semiconductor thin film in accordance with the present invention.

In accordance with still another aspect of the present invention, there is provided an organic solar cell comprising one or more polycyclic aromatic organic semiconductor compounds in accordance with the present invention or an organic semiconductor thin film in accordance with the present invention.

In accordance with still another aspect of the present invention, there is provided an organic light emitting diode comprising one or more polycyclic aromatic organic semiconductor compounds in accordance with the present invention or an organic semiconductor thin film in accordance with the present invention.

In accordance with still another aspect of the present invention, there is provided a sensor comprising one or more polycyclic aromatic organic semiconductor compounds in accordance with the present invention or an organic semiconductor thin film in accordance with the present invention.

In accordance with still another aspect of the present invention, there is provided an electronic, optical or electro-optical device comprising one or more polycyclic aromatic organic semiconductor compounds in accordance with the present invention or an organic semiconductor thin film in accordance with the present invention, which is selected from the group consisting of a thin film transistor (TFT), an integrated circuit component, a radio frequency identification (RFID) tag, an electronic light emitting display, a flat panel display, a backlight, a photodetector, a logic circuit, a memory device, a capacitor, a charge injecting layer, a Schottky diode, a planarising layer, an antistatic film, a conductive substrate or pattern, a photoconductor and an electrophotographic device.

MODE FOR INVENTION

Hereinafter, embodiments of the present invention will be described in detail with reference to the accompanying drawings. However, it would be understood by those skilled in the art that the present invention is not limited to the embodiments and various changes and modifications may be made without changing technical conception and essential features of the present invention. Thus, it is clear that the present invention is not limited to the following descriptions of embodiments.

Through the whole specification, the term "aromatic ring" includes at least one aromatic ring and the term "aromatic heterocyclic ring" includes at least one aromatic ring and at least one heterocyclic ring.

Through the whole specification, the term "heteroatom" denotes an element other than carbon and hydrogen and denotes an element selected from the group including, for example, but not limited to, N, O, S and P.

In accordance with an aspect of the present invention, there is provided a polycyclic aromatic organic semiconductor compound represented by the following formula 1:

[Formula 1]

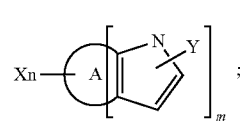

wherein in formula 1,

A is a ring selected from the group consisting of a substitutable 5-membered unsaturated or aromatic ring, a substitutable 6-membered unsaturated or aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group;

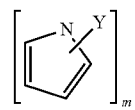

represents one or more pyrrol rings which may have a substituent Y, which is respectively fused with an end of A, and m is an integer of at least 1, Xn is a substituent independently selected from the following Substituent Group G1, which is bonded to A, and n is integer of 0 or at least 1:

<Substituent Group G1> the Substituent Group G1 consisting of a hydrogen, a halogen, a cyano group, a nitro group, a hydroxyl group, substituted or unsubstituted $C_1$-$C_{50}$ alkyl group, a substituted or unsubstituted $C_1$-$C_{50}$ alkoxy group, a substituted or unsubstituted $C_5$-$C_{50}$ cycloalkyl group, an substituted or unsubstituted $C_5$-$C_{50}$ heterocycloalkyl group, a substituted or unsubstituted $C_6$-$C_{50}$ aryl group, a substituted or unsubstituted $C_2$-$C_{50}$ heteroaryl group, an amine group, a carboxyl group, an acid anhydride, an ester group, a thiocarboxyl group, a dithiocarboxyl group, a sulfonic acid group, a sulfinic acid group, a sulfenic acid group, a sulfonyl group, a sulfinyl group, a, haloacyl group, a carbamoyl group, a hydrazide group, an imide group, an amide group, an amidino group, an isocyano group, a cyanic ester group, an isocyanic ester group, a thiocyanic ester group, an isothiocyanic ester group, a formyl group, a thioformyl group, an acyl group, a thiol group, an amino group, an imino group, a hydrazino group, an alkoxy group, an aryloxy group, an ether group, a sulfide group, disulfide group, an silyl group, a germyl group, a stanyl group, a hosphino group and a boryl group; or Xn represents one or more rings respectively fused with an end of A, and n is an integer of 0 or at least 1, in which X is a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group, in which each X may have one or more substituents selected from the Substituent Group G1; and Y is a substituent bonded to the pyrrol ring, being selected from the Substituent Group G1, or Y is a ring fused with the pyrrol ring, being a ring selected from the group consisting of a 5-membered aromatic ring, a substitutable 6-membered aromatic ring, a substitutable 5-membered unsaturated or aromatic heterocyclic ring, and a substitutable 6-membered unsaturated or aromatic heterocyclic ring, or a polycyclic ring formed by a fusion of two or more rings selected from the above group, in which Y may have one or more substituents selected from the Substituent Group G1.

The compound of the formula 1 is an organic semiconductor compound, in which at least one pyrrole ring is fused with an end of the ring A, having a conjugated electromagnetic field.

The substitutable 5-membered unsaturated ring defined as the ring A may be a 5-membered hydrocarbon ring including, for example, one or more carbon-carbon double bonds or triple bonds on the ring and may include all 5-membered unsaturated rings publicly known in the art and may include one or more substituents selected from the Substituent Group G1.

The substitutable 5-membered aromatic ring defined as the ring A may include all 5-membered aromatic rings publicly known in the art and may include one or more substituents selected from the Substituent Group G1.

The substitutable 6-membered unsaturated ring defined as the ring A may be a 6-membered hydrocarbon ring including, for example, one or more carbon-carbon double bonds or triple bonds on the ring and may include all 6-membered unsaturated rings publicly known in the art and may include one or more substituents selected from the Substituent Group G1.

The substitutable 6-membered aromatic ring defined as the ring A may be, for example, a benzene ring and may include one or more substituents selected from the Substituent Group G1.

The substitutable 5-membered unsaturated heterocyclic ring defined as the ring A may be a 5-membered hydrocarbon ring including one or more heteroatoms selected from the group including, for example, N, O, S and P as elements of the ring and one or more carbon-carbon double bonds or triple bonds on the ring and may include all 5-membered unsaturated heterocyclic rings publicly known in the art and may include one or more substituents selected from the Substituent Group G1.

The substitutable 5-membered aromatic heterocyclic ring defined as the ring A may be a 5-membered aromatic heterocyclic ring including one or more heteroatoms selected from the group including, for example, N, O, S and P as elements of the ring and may include all 5-membered aromatic heterocyclic rings publicly known in the art and may include one or more substituents selected from the Substituent Group G1. By way of example, the 5-membered aromatic heterocyclic ring may include, but is not limited to, a pyrrole ring, a furyl ring, a thiophenyl ring, a 1H-phosphol ring, an oxazole ring, an imidazole ring, an isoxazol ring, a thiazole ring, a thiadiazole ring, a thiatriazole ring, an azaphosphol ring, a diazaphosphol ring, an oxaphosphol ring, a pyrazole ring, a triazole ring, and a tetrazole ring. By way of example, the 5-membered aromatic heterocyclic ring may be, but is not limited to, a pyrrole ring.

The substitutable 6-membered aromatic heterocyclic ring defined as the ring A may be a 6-membered aromatic heterocyclic ring including one or more heteroatoms selected from the group including, for example, N, O, S and P as elements of the ring and may include all 6-membered aromatic heterocyclic rings publicly known in the art and may include one or more substituents selected from the Substituent Group G1. By way of example, the 6-membered aromatic heterocyclic ring may be, but is not limited to, a ring represented by the following formula 2:

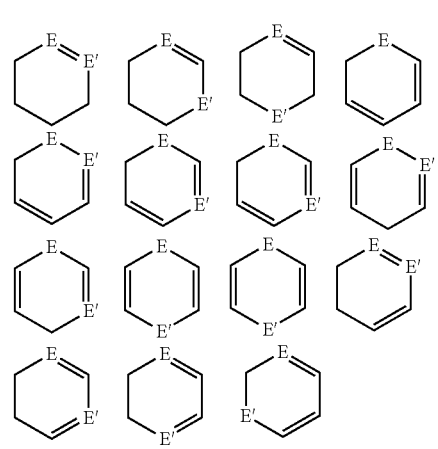

[Formula 2]

(Herein, E and E' may include $CR^{10}$, $C(R^1_0)_2$, N, $NR^{10}$, P, $PR^{10}$, O or S, and at least one of E and E' may be N, $NR^{10}$, P, $PR^{10}$, O or S, and $R^{10}$ may be a substituent such as H, an alkyl group, an alkenyl group, an alkynyl group and an alkoxy group.)

The substitutable 6-membered aromatic heterocyclic ring defined as the ring A may be a 6-membered aromatic heterocyclic ring including one or more heteroatoms selected from the group including, for example, N and P as elements of the ring and may include all 6-membered aromatic heterocyclic rings publicly known in the art and may include one or more substituents selected from the Substituent Group G1. By way of example, the 6-membered aromatic heterocyclic ring may include, but is not limited to, pyridine, pyridazine, pyrazine, triazihe, pyrimidine, phosphinine, diphosphinine, azaphosphinine, azadiphosphinine, and diazaphosphinine.

The ring A may include a ring selected from the group including the substitutable 5-membered unsaturated or aromatic ring, the substitutable 6-membered unsaturated or aromatic ring, the substitutable 5-membered unsaturated or aromatic heterocyclic ring, and the substitutable 6-membered unsaturated or aromatic heterocyclic ring, or a polycyclic ring formed by a fusion of two or more rings selected from the group at a position where two or more rings can be fused with each other. The ring A may include, but is not limited to, the following examples: a ring selected from the group including a benzene ring, a toluene ring, a naphthalene ring, an antracene ring, a phenanthrene ring, a pentalene ring, an inden ring, a biphenylene ring, a phenalene ring, an azulene ring, a heptalene ring, an acenaphthylene ring, a fluorene ring, a tetracene ring, a triphenylene ring, a pyrene ring, a chrysene ring, an ethyl-chrysene ring, a phycene ring, a perylene ring, a pentaphene ring, a pentacene ring, a tetraphenylene ring, a hexaphene ring, a hexacene ring, a rubicene ring, a coronene ring, a trinaphthylene ring, a heptaphene ring, a heptacene ring, a pyrantren ring, an ovalene ring, a fluoranthene ring, a benzofluoranthene ring and derivatives thereof; a ring selected from the group including a pyrrole ring, a furyl ring, a thiophenyl ring, a 1H-phosphol ring, an oxazole ring, an imidazole ring, an isoxazol ring, a thiazole ring, a thiadiazole ring, a thiatriazole ring, an azaphosphol ring, a diazaphosphol ring, an oxaphosphol ring, a pyrazole ring, a triazole ring, a tetrazole ring, a pyridine ring, a pyridazine ring, a pyrazine ring, a triazine ring, a pyrimidine ring, a phosphinine ring, a diphosphinine ring, an azaphosphinine ring, an azadiphosphinine ring, a diazaphosphinine ring, an indole ring, an isoindolyl ring, a benzofuran ring, an isobenzofuranyl ring, a quinolyl ring, an isoquinolyl ring, a quinoxalynyl ring, a carbazole ring, a phenanthridine ring, an acridine ring, a phenanthroline ring, a 1,7-phenanthroline ring, a 1,8-phenanthroline ring, a 1,10-phenanthroline ring, a 2,9-phenanthroline ring, a 2,8-phenanthroline ring, a 2,7-phenanthroline ring, a 1-phenazine ring, a 2-phenazine ring, a 1-phenothiazine ring, a 2-phenothiazine ring, a 3-phenothiazine ring, a 4-phenothiazine ring, a 10-phenothiazine ring, a 1-phenoxadine ring, a 2-phenoxadine ring, a 3-phenoxadine ring, a 4-phenoxadine ring, a 10-phenoxadine ring, a 2-oxazolyl ring, a 4-oxazolyl ring, a 5-oxazolyl ring, a 2-oxadiazolyl ring, a 5-oxadiazolyl ring, a 3-furazane ring, a 2-thienyl ring, a 3-thienyl ring and derivatives thereof; the following ring or a ring formed by a fusion of two or more rings selected from the following rings; and, a ring formed by a fusion of one or more of the following rings and one or more of the above-described rings:

[Formula 3]

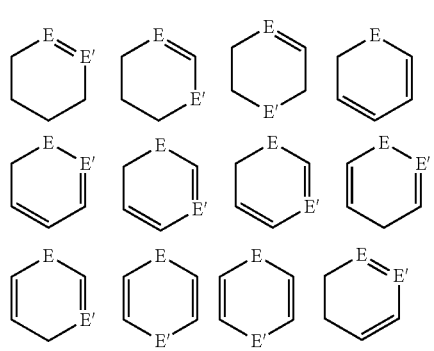

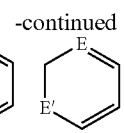

(Herein, E and E' may include $CR^{10}$, $C(R^{10})_2$, N, $NR^{10}$, P, $PR^{10}$, O or S, and at least one of E and E' may be N, $NR^{10}$, P, $PR^{10}$, O or S, and $R^{10}$ may be a substituent such as H, an alkyl group, an alkenyl group, an alkynyl group and an alkoxy group.)

The term "derivative" denotes the above-mentioned ring of which hydrogen is substituted by the above-described substituent or a heterocyclic ring having a heteroatom positioned differently.

The term "alkyl group" described in the present specification or the term "substituted or unsubstituted $C_1$-$C_{50}$ alkyl groups" of the Substituent Group G1 may include, for example, but not limited to, a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihdyroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisobpropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. By way of example, the alkyl group may be, but is not limited to, substituted or unsubstituted $C_1$-$C_{10}$ alkyl groups.

The term "alkenyl group" or the term "alkynyl group" may include the above-described examples of the alkyl group including a carbon-carbon double bond or triple bond. By way of example, the alkenyl group may be, but is not limited to, substituted or unsubstituted $C_2$-$C_{10}$ alkenyl groups or alkynyl groups.

The term "alkoxy group" described in the present specification and the term "substituted or unsubstituted $C_1$-$C_{50}$ alkoxy groups" of the Substituent Group G1 may be expressed with —OR' and the R' may include, but not limited to the above-described examples of the alkyl group. Desirably, the alkoxy group may be, but is not limited to, substituted or unsubstituted $C_1$-$C_{10}$ alkoxy groups.

In the Substituent Group G1, the substituted or unsubstituted $C_3$-$C_{50}$ cycloalkyl group may be, desirably, ($C_{3-12}$) cycloalkyl and to be specific, the substituted or unsubstituted $C_3$-$C_{50}$ cycloalkyl group may include cyclopropyl, cyclobutyl, cyclopentyl, cyclohexyl, cyclohexenyl, cycloheptyl, cycloheptenyl, cyclooctyl, cyclooctenyl, 2,5-cyclohexadienyl, bicyclo[2.2.2]octyl, adamant-1-yl, decahydronaphthyl, oxocyclohexyl, dioxocyclohexyl, thiocyclohexyl, and 2-oxobicyclo[2.2.1]hept-1-yl.

In the Substituent Group G1, the substituted or unsubstituted $C_2$-$C_{50}$ heterocycloalkyl group may be, desirably, hetero($C_{3-12}$)cycloalkyl and may include, but is not limited to, piperidyl, 4-morpholyl, 4-piperazinyl, pyrrolidinyl, perhydropyrrolidinyl, 1,4-diazaperhydroephynyl, 1,3-dioxanyl, and 1,4-dioxanyl.

In the Substituent Group G1, the substituted or unsubstituted $C_6$-$C_{50}$ aryl group may be selected from the group including, but not limited to, a benzene ring, a toluene ring, a naphthalene ring, an antracene ring, a phenanthrene ring, a pentalene ring, an inden ring, a biphenylene ring, a phenalene ring, an azulene ring, a heptalene ring, an acenaphthylene ring, a fluorene ring, a tetracene ring, a triphenylene ring, a pyrene ring, a chrysene ring, an ethyl-chrysene ring, a phycene ring, a perylene ring, a pentaphene ring, a pentacene ring, a tetraphenylene ring, a hexaphene ring, a hexacene ring, a rubicene ring, a coronene ring, a trinaphthylene ring, a heptaphene ring, a heptacene ring, a pyrantren ring, an ovalene ring, a fluoranthene ring, a benzofluoranthene ring, a 9-anthryl group, a 2-anthryl group, a 9-phenanthryl group, a 2-phenanthry group, a 1-pyrenyl group, a chrycenyl group, a naphthacenyl group, a coronyl group and derivatives thereof.

In the substituent Group G1, the substituted or unsubstituted $C_5$-$C_{50}$ heteroaryl group may include, but is not limited to, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalynyl group, a 5-quinoxalynyl group, a 6-quinoxalynyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxadinyl group, a 2-phenoxadinyl group, a 3-phenoxadinyl group, a 4-phenoxadinyl group, a 10-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-methyl-1-indolyl group, a 2-t-butyl-3-indolyl group, and a 4-t-butyl-3-indolyl group.

The polycyclic aromatic compound represented by the formula 1 in accordance with the present invention may include the ring A fused with one or more pyrrol rings, so that a ring of the compound may have a n-conjugated electromagnetic field, and, thus, the polycyclic aromatic compound may have high crystallinity, property of a semiconductor, thermal stability and photochemical stability. Therefore, the compound represented by the formula 1 in accordance with the present invention can be used as an organic semiconductor.

In an embodiment in accordance with the present invention, the polycyclic aromatic organic semiconductor compound represented by the formula 1 of the present invention may be, but is not limited to, a compound represented by the following formula 4:

[Formula 4]

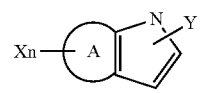

Herein, A, X and Y are the same as defined with respect to the formula 1, n is an integer of 0 or at least 1, for example, but not limited to, an integer of 0 or 1 to 6; or an integer of 0 or 1 to 4.

In the compound represented by the formula 4 in accordance with the embodiment of the present invention, if the X is a ring fused with the ring A, each X may be a ring defined with respect to the X of the formula 1 and desirably, may be an unsaturated ring, aryl or heteroaryl.

In the compound represented by the formula 4, the ring A is the same as defined or exemplified with respect to the formula 1. By way of example, the ring A may be a ring selected from the group including all substitutable 5-membered unsaturated rings, substitutable 6-membered unsaturated or aromatic rings, substitutable 5-membered unsaturated or aromatic heterocyclic rings and substitutable 6-membered unsaturated or aromatic heterocyclic rings or a polycyclic ring formed by a fusion one or more rings selected from the group at a position where two or more rings can be fused with each other. The ring A may be, but is not limited to, the following unsaturated ring, an aryl ring and a heteroaryl ring: a ring selected from the group including a benzene ring, a toluene ring, a naphthalene ring, an antracene ring, a phenanthrene ring, a pentalene ring, an inden ring, a biphenylene ring, a phenalene ring, an azulene ring, a heptalene ring, an acenaphthylene ring, a fluorene ring, a tetracene ring, a triphenylene ring, a pyrene ring, a chrysene ring, an ethyl-chrysene ring, a phycene ring, a perylene ring, a pentaphene ring, a pentacene ring, a tetraphenylene ring, a hexaphene ring, a hexacene ring, a rubicene ring, a coronene ring, a trinaphthylene ring, a heptaphene ring, a heptacene ring, a pyrantren ring, an ovalene ring, a fluoranthene ring, a benzofluoranthene ring and derivatives thereof; a ring selected from the group including a pyrrole ring, a furyl ring, a thiophenyl ring, a 1H-phosphol ring, an oxazole ring, an imidazole ring, an isoxazol ring, a thiazole ring, a thiadiazole ring, a thiatriazole ring, an azaphosphol ring, a diazaphosphol ring, an oxaphosphol ring, a pyrazole ring, a triazole ring, a tetrazole ring, a pyridine ring, a pyridazine ring, a pyrazine ring, a triazine ring, a pyrimidine ring, a phosphinine ring, a diphosphinine ring, an azaphosphinine ring, an azadiphosphinine ring, a diazaphosphinine ring, an indole ring, an isoindolyl ring, a benzofuran ring, an isobenzofuranyl ring, a quinolyl ring, an isoquinolyl ring, a quinoxalynyl ring, a carbazole ring, a phenanthridine ring, an acridine ring, a phenanthroline ring, a 1,7-phenanthroline ring, a 1,8-phenanthroline ring, a 1,10-phenanthroline ring, a 2,9-phenanthroline ring, a 2,8-phenanthroline ring, a 2,7-phenanthroline ring, a 1-phenazine ring, a 2-phenazine ring, a 1-phenothiazine ring, a 2-phenothiazine ring, a 3-phenothiazine ring, a 4-phenothiazine ring, a 10-phenothiazine ring, a 1-phenoxadine ring, a 2-phenoxadine ring, a 3-phenoxadine ring, a 4-phenoxadine ring, a 10-phenoxadine ring, a 2-oxazolyl ring, a 4-oxazolyl ring, a 5-oxazolyl ring, a 2-oxadiazolyl ring, a 5-oxadiazolyl ring, a 3-furazane ring, a 2-thienyl ring, a 3-thienyl ring and derivatives thereof; the following ring or a ring formed by a fusion of two or more rings selected from the following rings; and a ring formed by a fusion of one or more of the following rings and one or more of the above-described rings:

[Formula 3]

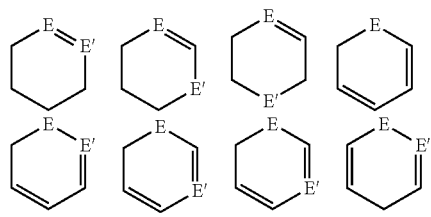

-continued

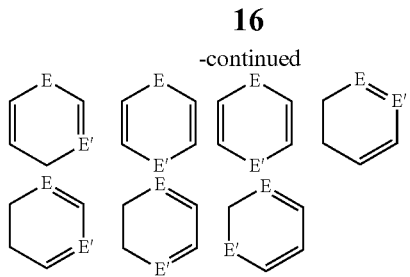

(Herein, E and E' may include $CR^{10}$, $C(R^{10})_2$, N, $NR^{10}$, P, $PR^{10}$, O or S, and at least one of E and E' may be N, $NR^{10}$, P, $PR^{10}$, O or S, and $R^{10}$ may be a substituent such as H, an alkyl group, an alkenyl group, an alkynyl group and an alkoxy group.)

In an embodiment of the present invention, the polycyclic aromatic organic semiconductor compound represented by the formula 4 of the present invention may be, but is not limited to, a compound represented by the following formula 5:

[Formula 5]

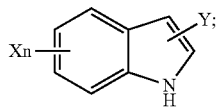

wherein, Y and X are the same as defined with respect to the formula 1, and n is 0, 1, 2, 3 or 4.

In an embodiment of the present invention, the polycyclic aromatic organic semiconductor compound represented by the formula 5 of the present invention may be, but is not limited to, a compound represented by the following formulas 6:

[Formula 6a]

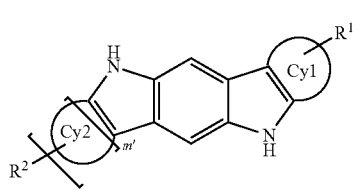

[Formula 6b]

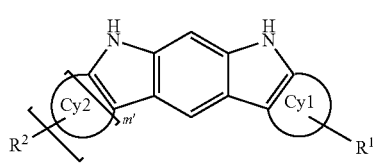

[Formula 6c]

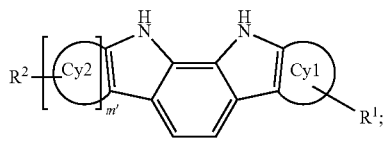

wherein, each of the rings Cy1 and Cy2 is a ring fused with the pyrrol ring and may be, for example, an unsaturated ring, an aryl ring or a heteroaryl ring exemplified with respect to the ring A; m' is 0 or 1; and $R^1$ and $R^2$ are identical with each other or different from each other and they are the same as the Y defined with respect to the formula 1.

The rings Cy1 and Cy2 may be, for example, unsaturated rings, aryl rings or heteroaryl rings exemplified with respect to the ring A.

In an embodiment of the present invention, the polycyclic aromatic organic semiconductor compound represented by the formulas 6 of the present invention may be, but is not limited to, the following compound:

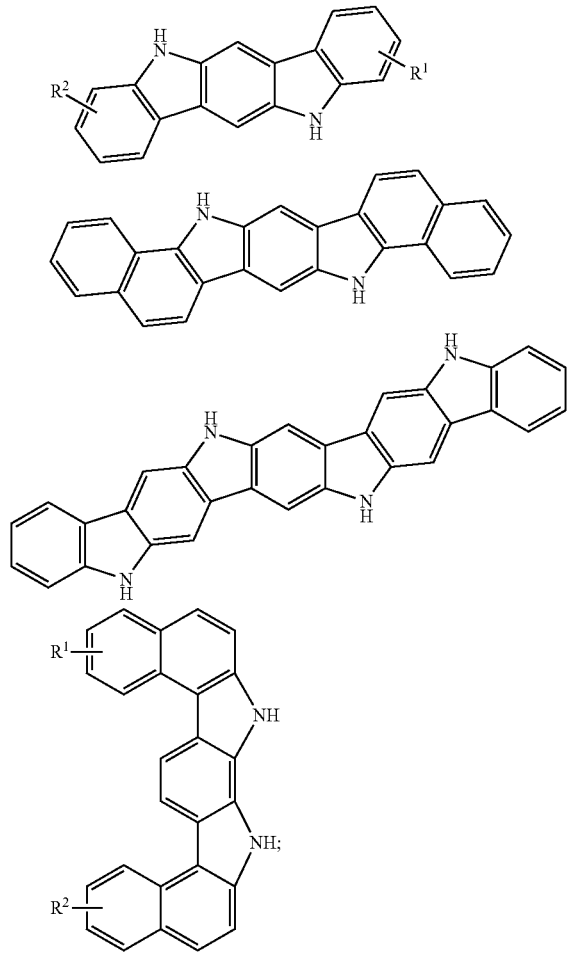

wherein, the $R^1$ and $R^2$ are the same as defined above.

In another embodiment of the present invention, the polycyclic aromatic organic semiconductor compound represented by the formula 5 of the present invention may be, but is not limited to, a compound represented by the following formulas 7:

[Formula 7a]

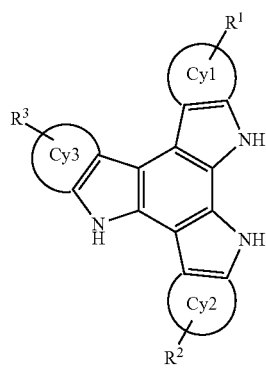

[Formula 7b]

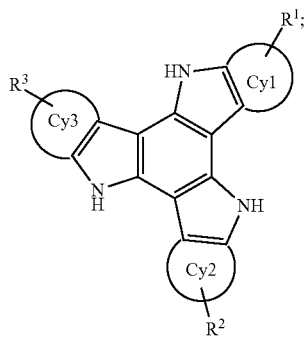

wherein, each of the rings Cy1, Cy2 and Cy3 is a ring fused with the pyrrol ring and may include, for example, the examples of the ring A, and $R^1$, $R^2$ and $R^3$ are identical with one another or different from one another and they are the same as the Y defined with respect to the formula 1.

In an embodiment of the present invention, the polycyclic aromatic organic semiconductor compound represented by the formulas 7 of the present invention may be, but is not limited to, the following compound:

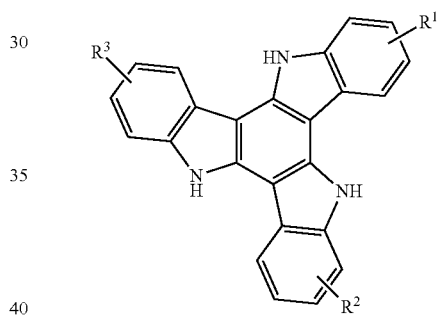

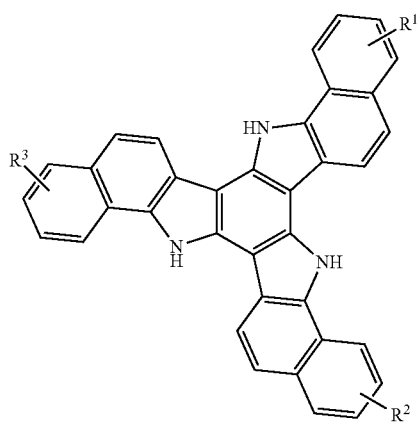

-continued

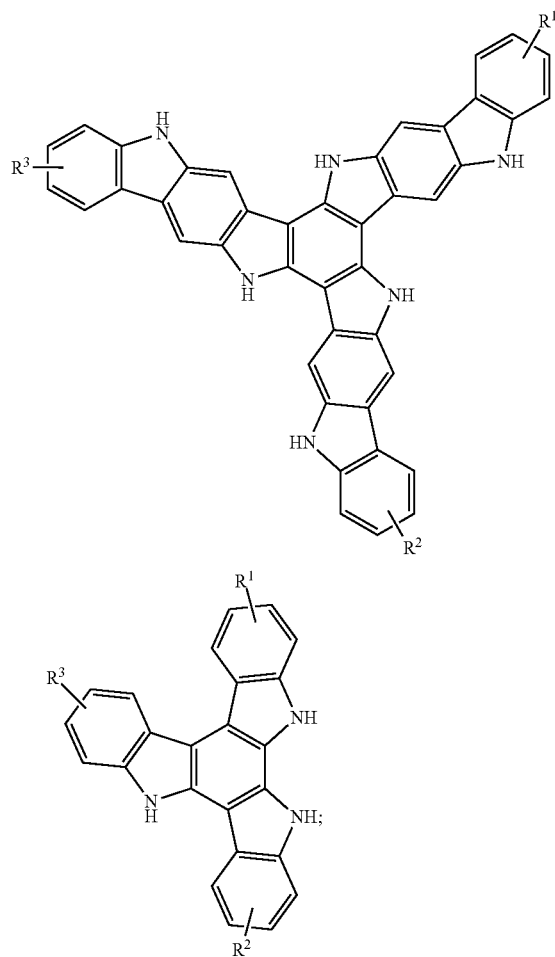

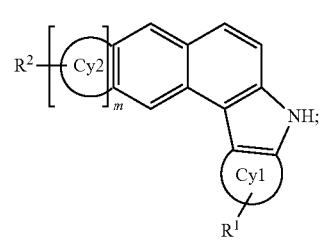

[Formula 9]

wherein, m is 0 or 1, and the rings Cy1 and Cy2 and $R^1$ and $R^2$ are the same as defined above.

In an embodiment of the present invention, the polycyclic aromatic organic semiconductor compound represented by the formula 8 of the present invention may be, but is not limited to, the following compound:

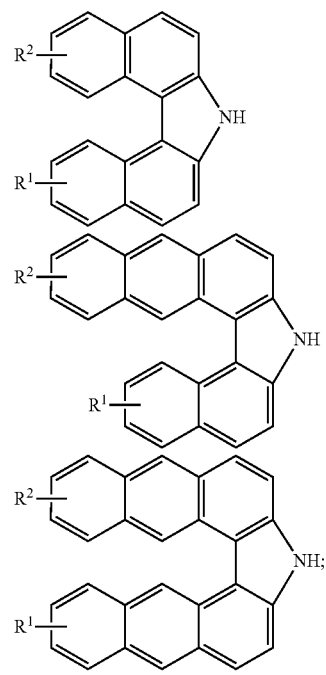

wherein, the $R^1$, $R^2$ and $R^3$ are the same as defined above.

In another embodiment of the present invention, the polycyclic aromatic organic semiconductor compound represented by the formula 1 of the present invention may be, but is not limited to, a compound represented by the following formula 10:

wherein, the $R^1$, $R^2$ and $R^3$ are the same as defined above.

In another embodiment of the present invention, the polycyclic aromatic organic semiconductor compound represented by the formula 1 of the present invention may be, but is not limited to, a compound represented by the following formula 8:

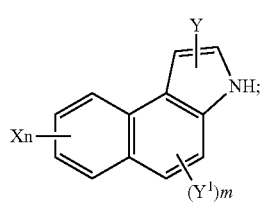

[Formula 8]

wherein, Y and X are the same as defined with respect to the formula 1, $Y^1$ is the same as the Y defined with respect to the formula 1, Y and $Y^1$ may be identical with one another or different from one another, m is 0 or 1, and n is 0, 1, 2, 3 or 4.

In an embodiment of the present invention, the polycyclic aromatic organic semiconductor compound represented by the formula 8 of the present invention may be, but is not limited to, a compound represented by the following formula 9.

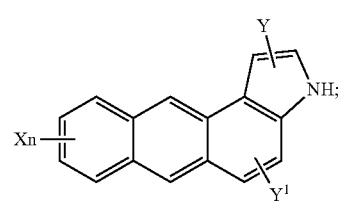

[Formula 10]

wherein, the Y, $Y^1$ and Xn are the same as defined above, and n is 0, 1, 2, 3 or 4.

In another embodiment of the present invention, the polycyclic aromatic organic semiconductor compound represented by the formula 1 of the present invention may be, but is not limited to, a compound represented by the following formula 11:

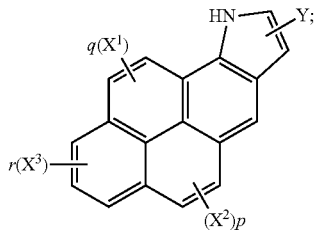

[Formula 11]

wherein, the Y is the same as defined above, $X^1$, $X^2$ and $X^3$ are identical with one another or different from one another, each of $X^1$, $X^2$ and $X^3$ is the same as defined with respect to the X, and p, q or r is 0, 1, 2 or 3 independently.

In another embodiment of the present invention, the polycyclic aromatic organic semiconductor compound represented by the formula 1 of the present invention may be, but is not limited to, a compound represented by the following formula 12:

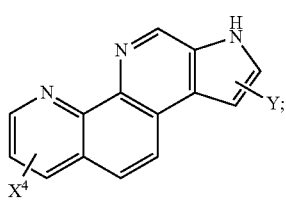

[Formula 12]

wherein, the Y is the same as defined above and $X^4$ is the same as defined with respect to the X.

In another embodiment of the present invention, the polycyclic aromatic organic semiconductor compound represented by the formula 1 of the present invention may be, but is not limited to, a compound represented by the following formula 13:

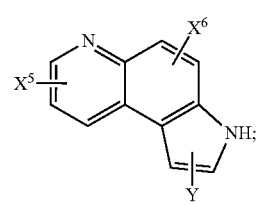

[Formula 13]

wherein, the Y is the same as defined with respect to the Y with respect to the formula 1, $X^5$ and $X^6$ are identical with each other or different from each other and may be the same as defined with respect to the X.

In another embodiment of the present invention, the polycyclic aromatic semiconductor represented by the formulas 1 to 13 of the present invention is shown in the following description and, but the following compounds do not limit the present invention:

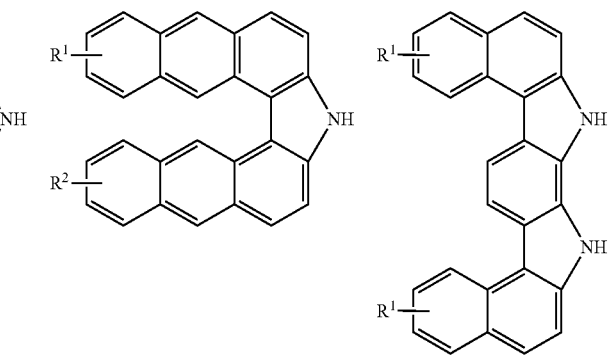

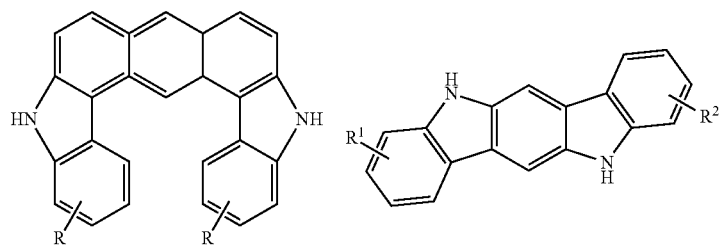

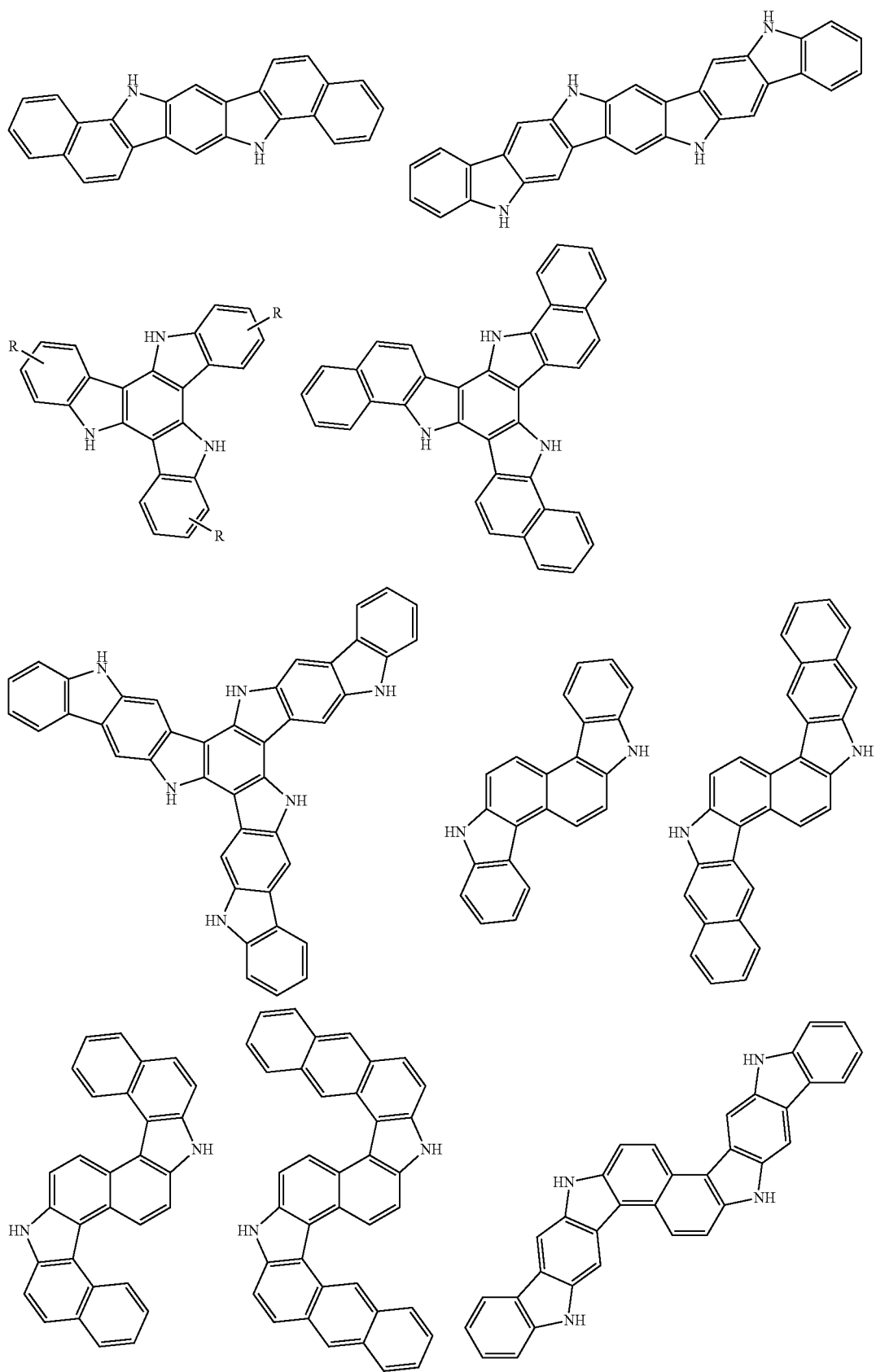

-continued
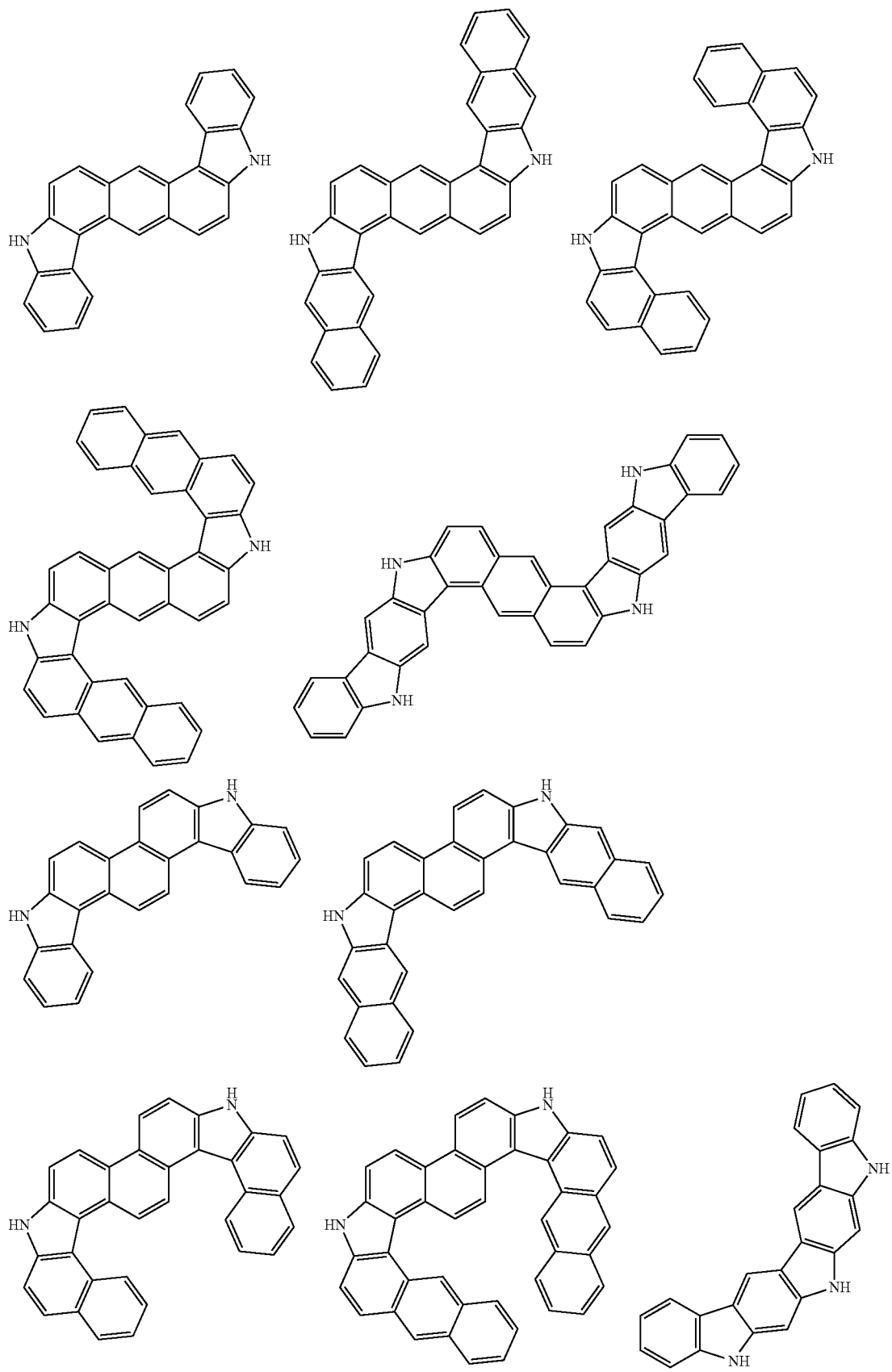

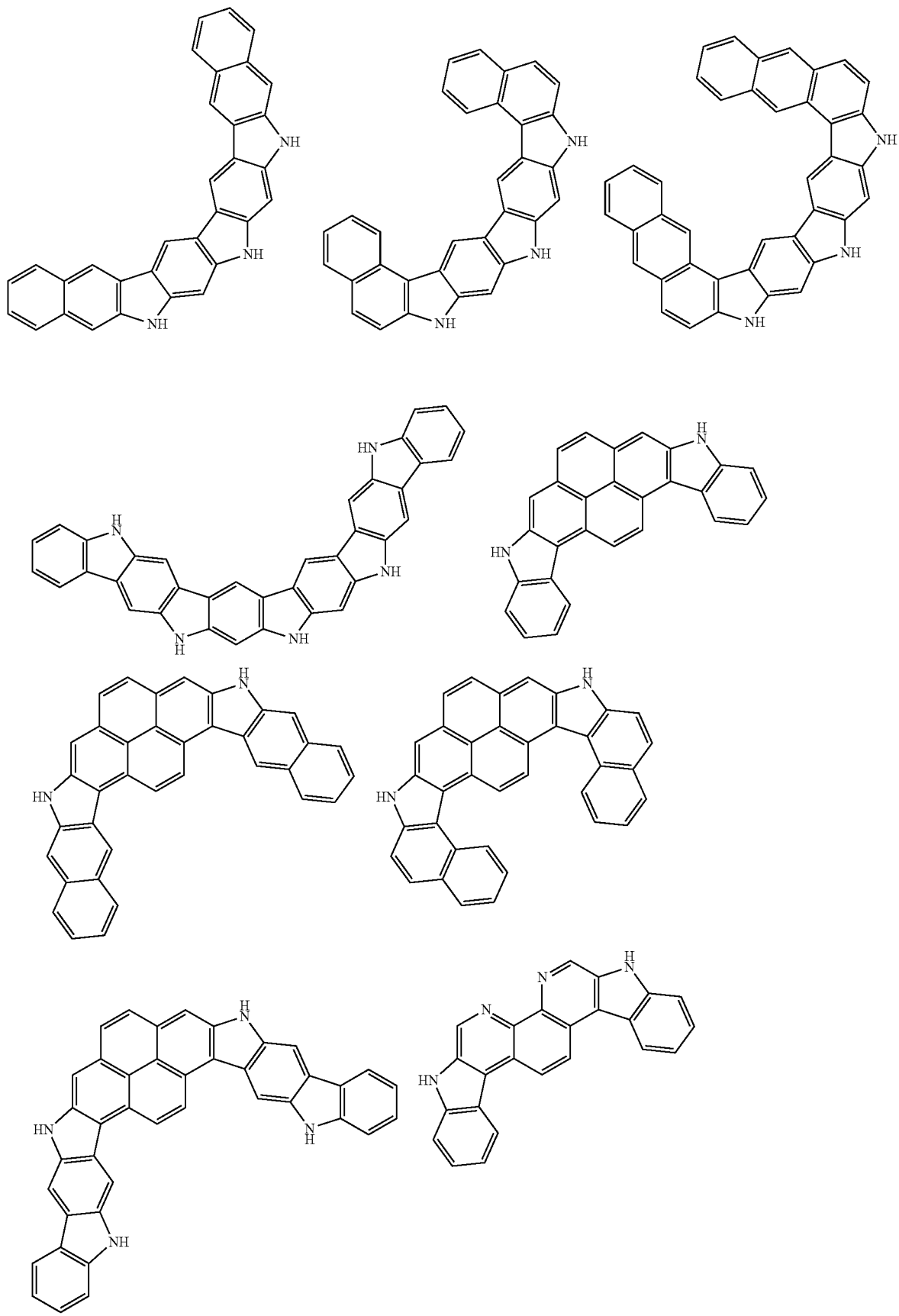

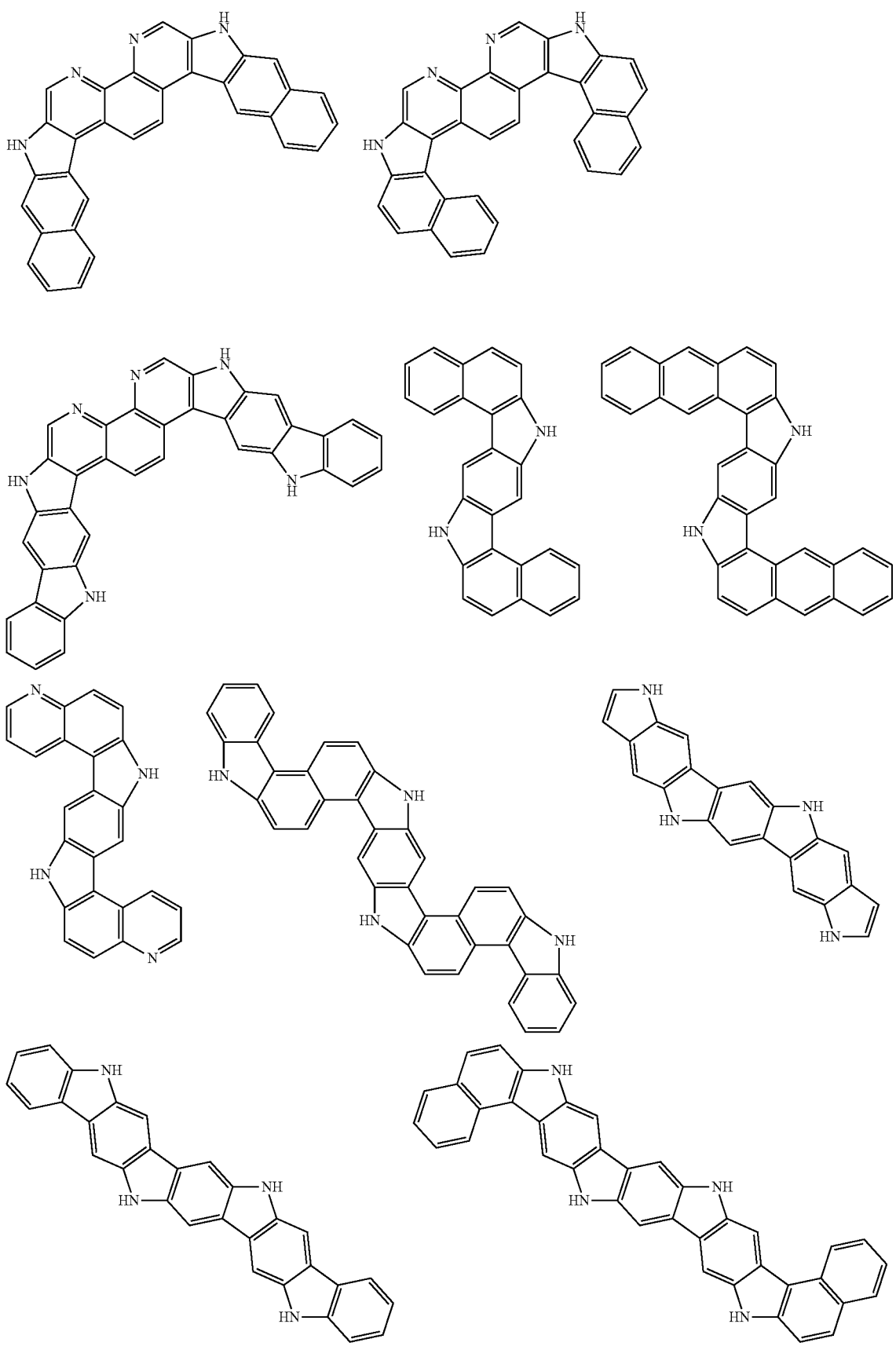

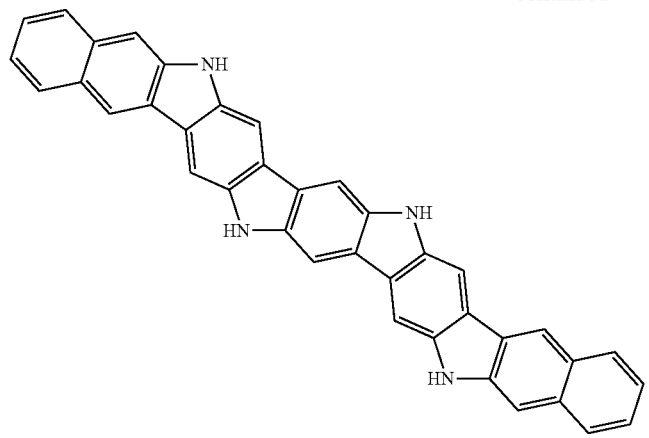
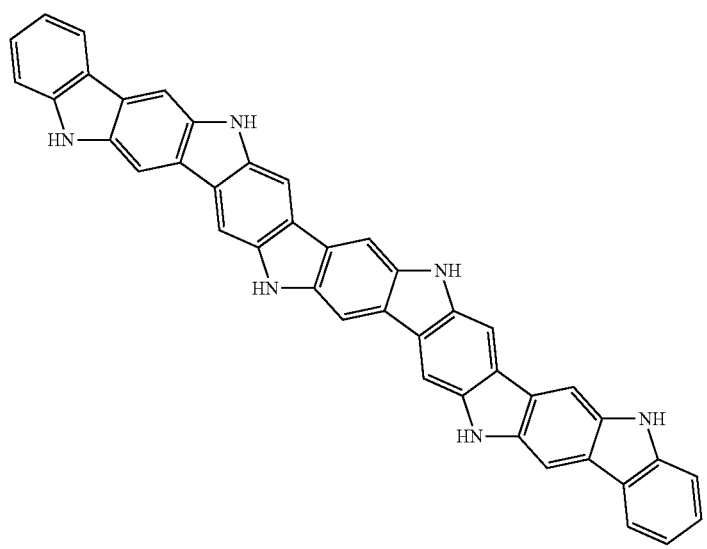
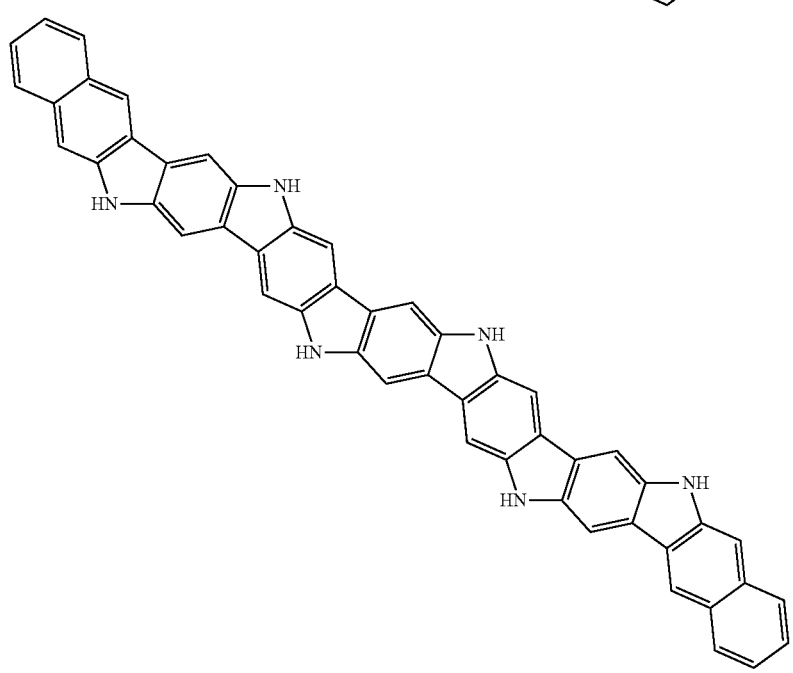

33 34
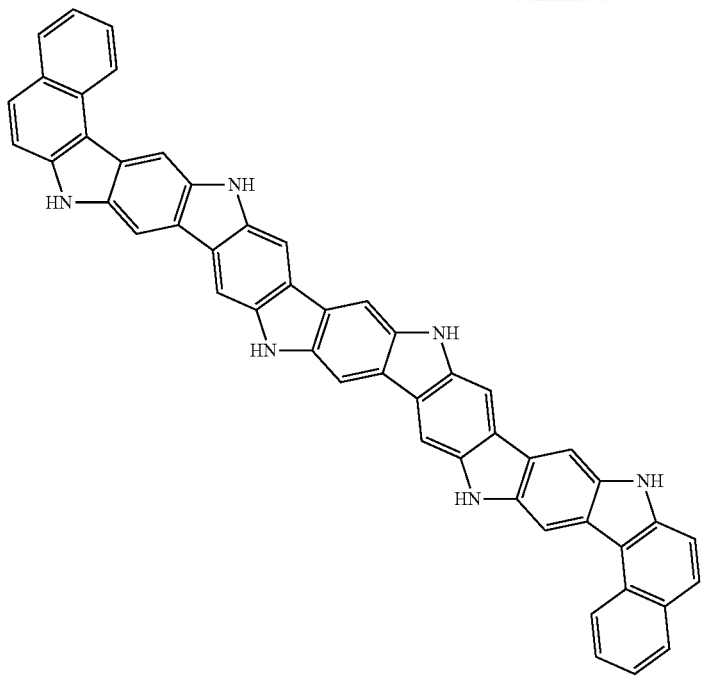
-continued

-continued

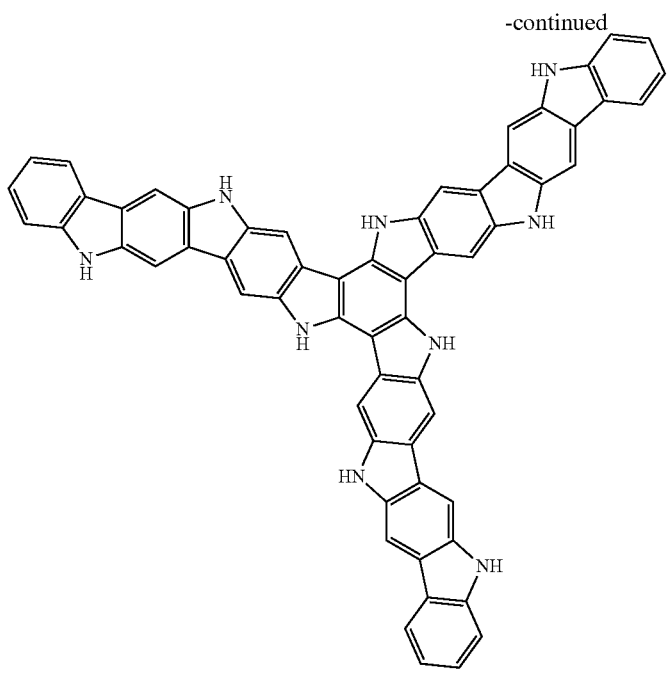

The polycyclic aromatic organic semiconductor compound represented by the formulas 1 to 13 in accordance with the present invention can be synthesized by using conventional synthesis and more detailed synthesis path of the compound can be seen from a reaction formula of the following synthesis examples.

In accordance with another aspect of the present invention, there is provided a method of preparing the novel polycyclic aromatic organic semiconductor compound in accordance with the present invention. To be specific, the present invention provides an effective synthesis method of a polycyclic aromatic compound containing nitrogen as a practical synthesis method.

Various methods for effectively synthesizing a polycyclic aromatic compound containing a substituent described above have been suggested. About one hundred years ago, a relevant technique called as Fischer indole synthesis was published (Org. Prep. Proced. Int. 1933, 25, 609). The present inventors have improved such synthesis and achieved a novel method using hydrazine. As can be seen from the following two reaction formulas, aryl hydrazide reacted with a keton compound to produce one or more indole. It has been found that if nitrogen is substituted by a functional group of Boc(t-butyloxycarbonyl), the reaction proceeded very readily:

It can be found that the reaction proceeds with high efficiency in the presence of an acid such as HCl to form a polycyclic structure by forming hydrazine at both sides of benzene like a compound 4 as shown in the following reaction formula:

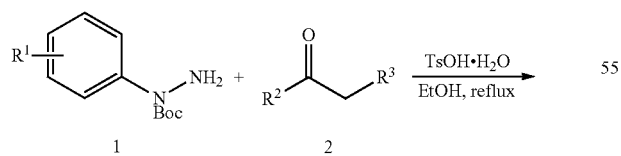

6: Z = H, 14%,
7: Z = Boc, 3%,

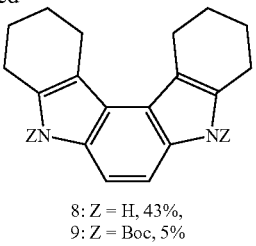

8: Z = H, 43%,
9: Z = Boc, 5%

In this case, in order to improve the effect, as can be seen from the following reaction formula, a new substituent instead of Boc is added to the nitrogen in the present invention. If a functional group of carbobenzyloxy (Cbz) is used, a transformation yield of about 95% or more can be obtained from a methanol solvent with a catalyst of sulfuric acid:

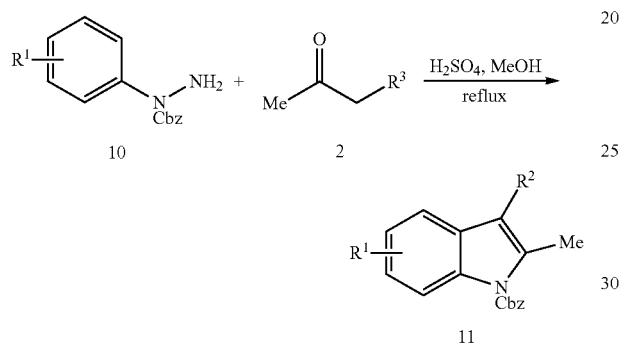

In a method of synthesizing carbazole more readily and economically with further improvement, as can be seen from the following reaction formula, if hydrazide having a functional group of Cbz at a position of nitrogen reacts with cyclohexanon, tetrahydro-N-Cbz can be produced and this tetrahydro-N-Cbz reacts with an oxidizer such as 2,3-dichloro-5,6-dicyano-1,4-benzoquinone (DDQ), so that N-Cbz-carbazole can be produced with a very high yield:

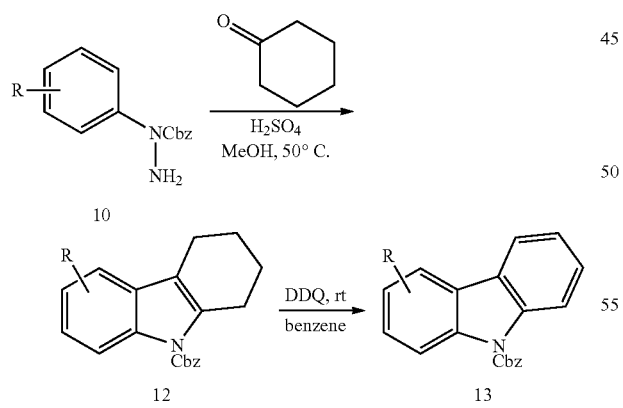

This method has been employed to produce a pyrro[2,3-f] indole system. As can be seen from the following reaction formula, 1,4-diiodobenzene reacts with benzyl carbazate in the presence of a catalyst of Cu(I) to produce bis-hydrazide and this bis-hydrazide reacts with keton, so that pyrro[2,3-f] indole and pyrro[3,3-e]indole can be synthesized economically with a high yield:

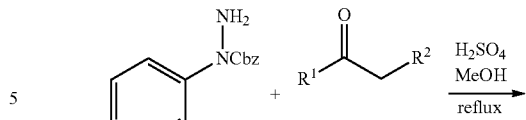

14    2

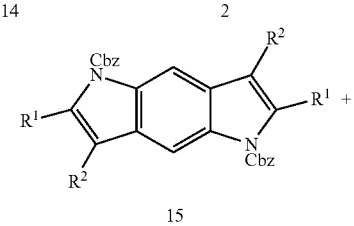

15

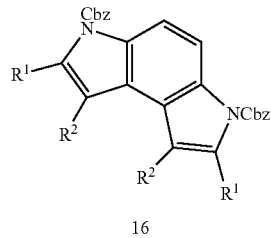

16

Further, the present inventors have achieved new methods of synthesizing a polycyclic aromatic compound by making reactions with aryl hydrazine, aryl hydrazide, keton, aldehyde and acetal. In accordance with this new method, various polycyclic aromatic compounds can be synthesized and a large quantity of compounds can be synthesized economically with high purity.

Thus, in an embodiment of the present invention, the polycyclic aromatic organic semiconductor compound represented by the formula 1 in accordance with the present invention can be prepared by a preparing method including a reaction between a compound represented by the following formula 1' and a compound represented by the following formula 2' in the presence of an acid:

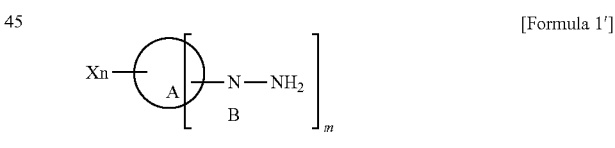

[Formula 1']

wherein A, Xn and m are the same as defined with respect to the formula 1; B is represented by —CO—O—R'$_3$; and R'$_3$ is a $C_1$-$C_{20}$ hydrocarbon group which includes one or more heteroatoms selected from the group including O, N and S;

$$R'_1—CO—CH_2—R'_2 \quad \text{[Formula 2']}$$

wherein each of R'$_1$ and R'$_2$ is hydrogen or a $C_1$-$C_{20}$ hydrocarbon group which may include one or more heteroatoms selected from the group including O, N and S, and R'$_1$ and R'$_2$ may together form at least 3-membered ring if R'$_1$ and R'$_2$ are $C_1$-$C_{20}$ hydrocarbon groups.

As a non-limiting example, R'$_3$ of B in the formula 1' may be, but is not limited to, methyl, ethyl, propyl, t-butyl or benzyl.

Thermal stability of a polycyclic aromatic organic semiconductor compound represented by the formula 1 in accordance with the present invention can be obtained by measuring decomposition temperature (Td) and melting temperature (Tm) of the compound through thermal analysis using thermo gravimetric analysis (TGA) and differential scanning calorimetry (DSC). The polycyclic aromatic organic semiconductor compounds represented by the formula 1 in accordance with the present invention can be used as a polycyclic aromatic organic semiconductor having high thermal stability.

By evaluating a photoluminescence (PL) spectrum of polycyclic aromatic organic semiconductor compounds represented by the formula 1 in accordance with the present invention, it is possible to evaluate a luminescence property of each compound. By way of example, a luminescence property of the polycyclic aromatic organic semiconductor compound in accordance with the present invention can be evaluated in a solution by using an appropriate solvent, and the polycyclic aromatic organic semiconductor compound in accordance with the present invention shows an excellent luminescence property from a visible light range to an infrared light range.

Crystallinity of a polycyclic aromatic organic semiconductor compound represented by the formula 1 in accordance with the present invention is similar to crystallinity of pentacene.

In accordance with another aspect of the present invention, there is provided an organic semiconductor thin film including one or more polycyclic aromatic organic semiconductor compounds represented by the formula 1 in accordance with the present invention.

In accordance with another aspect of the present invention, there is provided an electronic, optical or electro-optical device including one or more polycyclic aromatic organic semiconductor compounds in accordance with the present invention or an organic semiconductor thin film containing the compound.

In this regard, in an embodiment of the present invention, there is provided an organic semiconductor device such as an organic field effect transistor (OFET) including one or more polycyclic aromatic organic semiconductor compounds in accordance with the present invention or an organic semiconductor thin film containing the compound.

In the present invention, the organic semiconductor device such the an organic field effect transistor may include a source/drain electrode, a channel forming area interposed or sandwiched between source/drain electrodes, a gate insulating layer, and a gate electrode installed to face the channel forming area via the gate insulating layer, and the channel forming area may be formed of the organic semiconductor thin film containing one or more polycyclic aromatic organic semiconductor compounds represented by the formula 1 of the present invention.

Herein, the organic field effect transistor in accordance with the present invention may have the following four kinds of structures.

That is, a first structure of the organic field effect transistor be a so-called bottom gate/bottom contact type organic field effect transistor and may include (A) a gate electrode formed on a base, (B) a gate insulating layer formed on the gate electrode and a base body, (C) a source/drain electrode formed on the gate insulating layer, and (D) a channel forming area formed of the organic semiconductor thin film of the present invention on the gate insulating layer between the source/drain electrodes.

Further, a second structure of the organic field effect transistor may be a so-called bottom gate/top contact type organic field effect transistor and may include (A) a gate electrode formed on a base body, (B) a gate insulating layer formed on the gate electrode and the base body, (C) a channel forming area formed of the organic semiconductor thin film of the present invention on the gate insulating layer, and (D) a source/drain electrode formed on the organic semiconductor thin film.

Furthermore, a third structure of the organic field effect transistor may be a so-called top gate/top contact type organic field effect transistor and may include (A) a channel forming area formed of the organic semiconductor thin film of the present invention on a base body, (B) a source/drain electrode formed on the organic semiconductor thin film, (C) a gate insulating layer formed on the source/drain electrode and the organic semiconductor thin film, and (D) a gate electrode formed on the gate insulating layer.

Moreover, a fourth structure of the organic field effect transistor may be a so-called top gate/bottom contact type organic field effect transistor and may include (A) a source/drain electrode formed on a base body, (B) a channel forming area formed of the organic semiconductor thin film of the present invention on the source/drain electrode and the base body, (C) a gate insulating layer formed on the organic semiconductor thin film, and (D) a gate electrode formed on the gate insulating layer.

A structure of the organic field effect transistor in accordance with the present invention and a preparing method thereof can be selected appropriately from those publicly known in the art by those skilled in the art. By way of example, it may be possible to refer to Patent Document [Korean Patent Laid-open Publication No. 10-2006-0125496] the entire disclosures of which are incorporated herein by reference.

In accordance with an embodiment of the present invention, there is provided the following organic light emitting device including one or more polycyclic aromatic organic semiconductor compounds in accordance with the present invention or an organic semiconductor thin film containing the compounds and a method of preparing the organic light emitting device may include the following steps: forming an organic thin film containing an organic light emitting compound represented by the formula 1 in accordance with the present invention on a first electrode; burning the organic thin film; and forming a second electrode on the organic thin film.

The organic thin film may be formed by using a wet emission method including vapor deposition, spin coating, inkjet printing and spray printing or a thermal transfer method.

The polycyclic aromatic organic semiconductor compounds of the formula 1 in accordance with the present invention are suitable to be used for an organic film, particularly a light emitting layer, an electron hole injection layer or an electron hole transfer layer of the organic light emitting device.

Unlike a conventional organic field effect light emitting device, manufactured by liquid coating, of which an organic film has low stability, an organic field effect light emitting device in accordance with the present invention includes an organic light emitting compound having high solubility and thermal stability and capable of forming a stable organic film and provides light emitting property improved in driving voltage, efficiency, color purity and brightness.

The organic light emitting device in accordance with the present invention has various structures. The organic light emitting device may further include one or more layers selected from the group including an electron hole injection layer, an electron hole transfer layer, an electron hole blocking layer, an electron blocking layer, an electron transfer layer, and an electron injection layer between the first electrode and the second electrode. To be more specific, in an embodiment in accordance with the present invention, the organic light emitting device may have a structure including a first electrode, an electron hole injection layer, a light emitting layer, an electron transfer layer, an electron injection layer, and a second layer, or a structure including a first electrode, an electron hole injection layer, an electron hole transfer layer, a light emitting layer, an electron transfer layer, an electron injection layer, and a second electrode, or a structure including a first electrode, an electron hole injection layer, an electron hole transfer layer, a light emitting layer, an electron hole blocking layer, an electron transfer layer, an electron injection layer, and a second layer. Herein, one or more of the light emitting layer, electron hole injection layer and electron hole transfer layer may contain the polycyclic aromatic organic semiconductor compound in accordance with the present invention.

A structure and a manufacturing method of the organic light emitting device in accordance with the present invention can be selected appropriately from those publicly known in the art by those skilled in the art. By way of example, it may be possible to refer to Patent Document [Korean Patent Laid-open Publication No. 10-2008-0047209] the entire disclosures of which are incorporated herein by reference.

By way of example, it may be possible to manufacture an organic light emitting device containing the polycyclic aromatic organic semiconductor compound represented by the formula 1 in accordance with the present invention by using the compound represented by the formula 1 as a dopant of a light emitting layer. The organic light emitting device may have a structure including ITO, -NPD (500 Å), the polycyclic aromatic organic semiconductor compound represented by the formula 1 in accordance with the present invention+ADN (500 Å), Alq3 (200 Å), LiF (10 Å), and Al (2000 Å). As an anode, 15 Ω/cm² (1000 Å) ITO glass substrate manufactured by Corning Inc. is used after being cut into 50 mm×50 mm×0.7 mm, ultrasonic-cleaned in each of acetone isopropyl alcohol and pure water for about 15 minutes and cleaned with UV/ozone for about 30 minutes. An electron hole injection layer of about 500 Å is formed by vacuum depositing N,N'-di(naphthalene-1-yl)-N,N'-diphenylbenzidine (-NPD) on the substrate. A light emitting layer of about 500 Å is formed by vacuum depositing the polycyclic aromatic organic semiconductor compound represented by the formula 1 in accordance with the present invention on the electron hole injection layer. An electron transfer layer is formed by vacuum depositing an organic complex (for example, tri-8-hydrozyquinolinato aluminum, Alq3 or the like) of about 200 Å on the light emitting layer. Further, an organic light emitting device is manufactured by vacuum depositing LiF (electron injection layer) of about 10 Å and Al (cathode) of about 2000 Å in sequence on the electron transfer layer. Driving voltage, brightness and efficiency of the manufactured organic light emitting layer is evaluated by using PR650 (Spectroscan) Source Measurement Unit.

In an embodiment of the present invention, there is provided an organic solar cell including one or more polycyclic aromatic organic semiconductor compounds in accordance with the present invention or an organic semiconductor thin film containing the compounds.

The organic solar cell including one or more polycyclic aromatic organic semiconductor compounds in accordance with the present invention or an organic semiconductor thin film containing the compounds can be manufactured by a method publicly known in the art and one or more polycyclic aromatic organic semiconductor compounds can be coated on a conductive substrate so as to be used as an active layer.

In an embodiment of the present invention, there is provided a sensor including one or more polycyclic aromatic organic semiconductor compounds in accordance with the present invention or an organic semiconductor thin film containing the compounds. One or more polycyclic aromatic organic semiconductor compounds in accordance with the present invention can be substituted for a conventional organic semiconductor compound used in various kinds of conventional semiconductor sensors, and a kind, a structure, and a manufacturing method of sensor can be selected appropriately by those skilled in the art.

In an embodiment of the present invention, there is provided a thin film transistor (TFT), an integrated circuit (IC) component, a radio frequency identification (RFID) tag, an electronic light emitting display, a flat panel display, a backlight, a photodetector, a logic circuit, a memory device, a capacitor, a PV cell, a charge injecting layer, a Schottky diode, a planarising layer, an antistatic film, a conductive substrate or pattern, a photoconductor or an electrophotographic device including one or more polycyclic aromatic organic semiconductor compounds in accordance with the present invention or an organic semiconductor thin film containing the compounds. Various devices as described above can be manufactured by using one or more polycyclic aromatic organic semiconductor compounds in accordance with the present invention, and a kind, a structure, a manufacturing method of a device can be selected appropriately by those skilled in the art.

Hereinafter, examples of the present invention will be provided but the present invention is not limited to the following examples.

EXAMPLES

Example 1

Synthesis of Compound No. 1

A compound No. 1 in accordance with the present invention was synthesized according to a reaction path of the following reaction formula 1:

[Reaction formula 1]

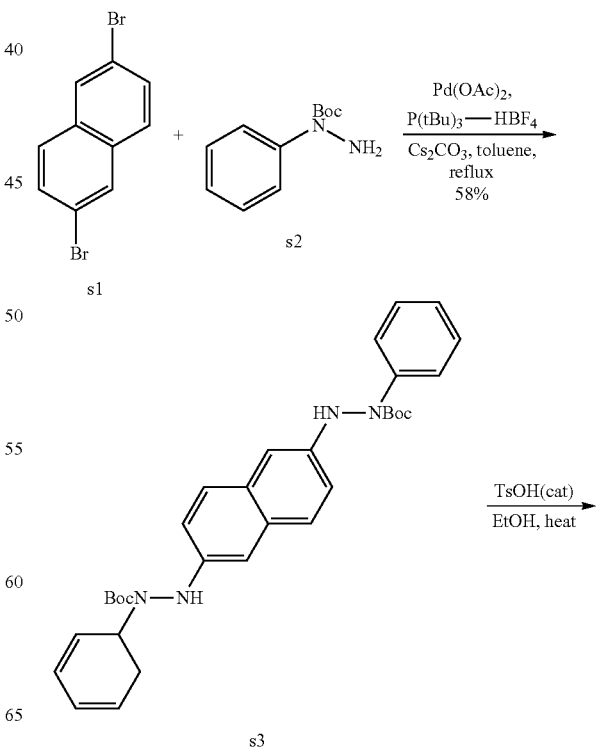

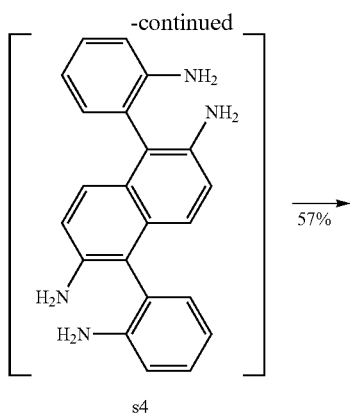

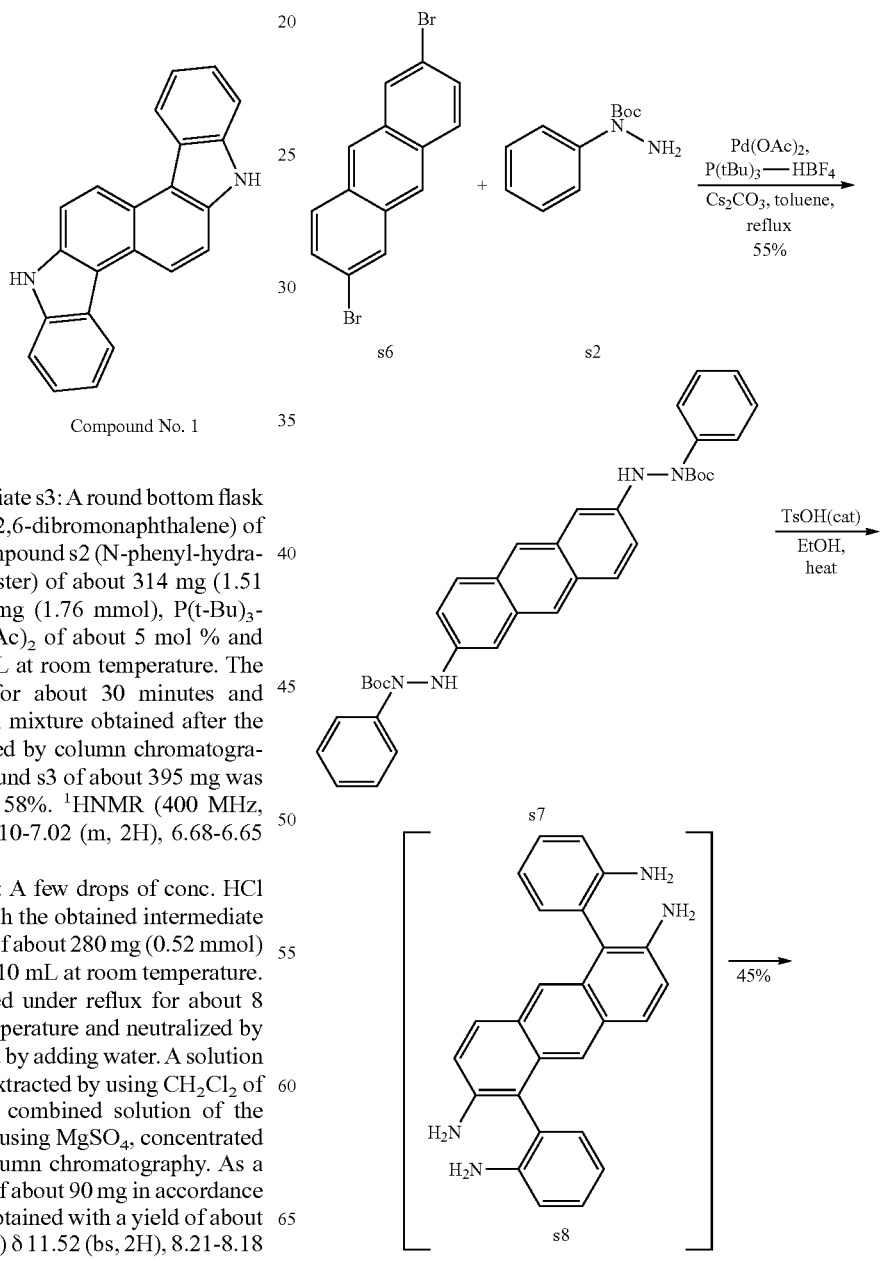

The above-described reactions can be carried out by reference to the following references:
1) Synthesis of compound s2 (N-phenyl-hydrazine carboxylic acid tert-butyl ester): Wolter, M.; Klapars, A.; Buchwald, S. L. *Org. Lett.* 2001, 3, 3803.
2) A general sequence for synthesis of diaryl hydrazaide and carbazole derivative: Lim, Y.-K.; Choi, S.; Park, K.-B.; Cho, C-G. *J. Org. Chem.* 2004, 69, 2603.

Example 2

Synthesis of Compound No. 2

A compound No. 2 in accordance with the present invention was synthesized according to a reaction path of the following reaction formula 2:

[Reaction formula 2]

Synthesis of reaction intermediate s3: A round bottom flask was filled with a compound s1 (2,6-dibromonaphthalene) of about 360 mg (1.26 mmol), a compound s2 (N-phenyl-hydrazine carboxylic acid tert-butyl ester) of about 314 mg (1.51 mmol), $Cs_2CO_3$ of about 573 mg (1.76 mmol), P(t-Bu)$_3$-HBF$_4$ of about 5 mol %, Pd(OAc)$_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s3 of about 395 mg was obtained with a yield of about 58%. $^1$HNMR (400 MHz, CDCl$_3$) δ 7.68-7.51 (m, 6H), 7.10-7.02 (m, 2H), 6.68-6.65 (m, 8H), 1.39 (s, 18H).

Synthesis of compound no. 1: A few drops of conc. HCl were added to a solution in which the obtained intermediate compound s3(diaryl hydrazide) of about 280 mg (0.52 mmol) was dissolved in EtOH of about 10 mL at room temperature. The reaction mixture was heated under reflux for about 8 hours, cooled down to room temperature and neutralized by adding NaHCO$_3$ and then diluted by adding water. A solution obtained after the reaction was extracted by using CH$_2$Cl$_2$ of about 50 mL several times. A combined solution of the extracted solutions was dried by using MgSO$_4$, concentrated and purified and isolated by column chromatography. As a result, a target compound No. 1 of about 90 mg in accordance with the present invention was obtained with a yield of about 57%. $^1$HNMR (400 MHz, CDCl$_3$) δ 11.52 (bs, 2H), 8.21-8.18 (m, 2H), 7.53-7.38 (m, 6H), 7.09-7.07 (m, 2H).

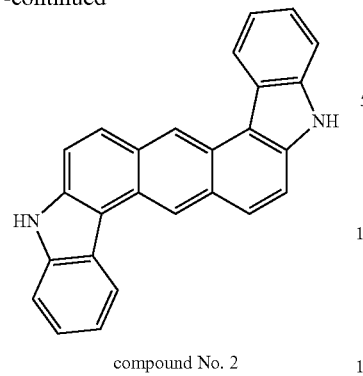

compound No. 2

Synthesis of reaction intermediate s7: A round bottom flask was filled with a compound s6 (2,6-dibromoanthracene) of about 444 mg (1.32 mmol), a compound s2 (N-phenyl-hydrazine carboxylic acid tert-butyl ester) of about 329 mg (1.55 mmol), $Cs_2CO_3$ of about 602 mg (1.85 mmol), $P(t-Bu)_3$-$HBF_4$ of about 5 mol %, $Pd(OAc)_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s7 of about 429 mg was obtained with a yield of about 55%. $^1$HNMR (400 MHz, $CDCl_3$) δ 8.01-6.78 (m, 14H), 6.40 (bs, 2H), 1.38 (s, 18H).

Synthesis of compound No. 2: A few drops of conc. HCl were added to a solution in which the obtained intermediate s7 (diaryl hydrazide) of about 320 mg (0.54 mmol) was dissolved in EtOH of about 10 mL at room temperature. The reaction mixture was heated under reflux for about 8 hours, cooled down to room temperature and neutralized by adding $NaHCO_3$ and then diluted by adding water. A solution obtained after the reaction was extracted by using $CH_2Cl_2$ of about 50 mL several times. A combined solution of the extracted solutions was dried by using $MgSO_4$, concentrated and purified and isolated by column chromatography. As a result, a target compound No. 2 of about 87 mg in accordance with the present invention was obtained with a yield of about 45%. $^1$HNMR (400 MHz, $CDCl_3$) δ 8.19-8.02 (m, 4H), 7.91-7.84 (m, 2H), 7.52-7.43 (m, 6H), 7.24-7.16 (m, 2H).

Example 3

Synthesis of Compound No. 3

A compound No. 3 in accordance with the present invention was synthesized according to a reaction path of the following reaction formula 3:

[Reaction formula 3]

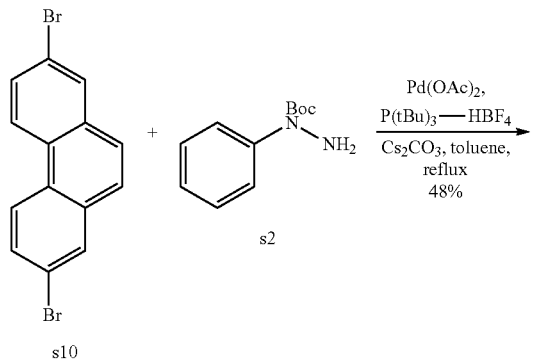

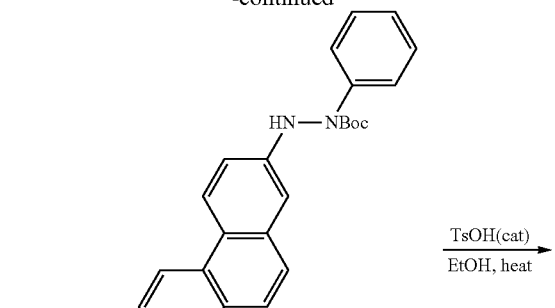

compound No. 3

Synthesis of reaction intermediate s11: A round bottom flask was filled with a compound s10 (2,7-dibromophenanthrene) of about 350 mg (1.04 mmol), a compound s2 (N-phenyl-hydrazine carboxylic acid tert-butyl ester) of about 260 mg (1.25 mmol), $Cs_2CO_3$ of about 476 mg (1.46 mmol), $P(t-Bu)_3$-$HBF_4$ of about 5 mol %, $Pd(OAc)_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s11 of about 295 mg was obtained with a yield of about 48%. $^1$HNMR (400 MHz, $CDCl_3$) δ 8.82-8.80 (m, 2H), 7.60-7.52 (m, 6H), 7.12-7.04 (m, 2H), 6.70-6.63 (m, 8H), 1.39 (s, 18H).

The synthesis of the compound s10 (2,7-dibromophenanthrene) can be carried out by reference to J. W.; Tour, J. M. *TetrahedronLett*. 2004, 45, 2801.

Synthesis of compound No. 3: A few drops of conc. HCl were added to a solution in which the obtained intermediate (diaryl hydrazide) of about 128 mg (0.22 mmol) was dissolved in EtOH of about 8 mL at room temperature. The reaction mixture was heated under reflux for about 8 hours, cooled down to room temperature and neutralized by adding NaHCO$_3$ and then diluted by adding water. A resultant solution was extracted by using CH$_2$Cl$_2$ of about 30 mL for various time periods. A combined solution of the extracted solutions was dried by using MgSO$_4$, concentrated and purified and isolated by column chromatography. As a result, a target compound No. 3 of about 36 mg in accordance with the present invention was obtained with a yield of about 46%. $^1$HNMR (400 MHz, CDCl$_3$) δ 11.52 (bs, 2H), 8.92-8.90 (m, 2H), 8.21-8.18 (m, 2H), 7.85-7.55 (m, 6H), 7.35-7.29 (m, 4H).

Example 4

Synthesis of Compound No. 4

A compound No. 4 in accordance with the present invention was synthesized according to a reaction path of the following reaction formula 4:

[Reaction formula 4]

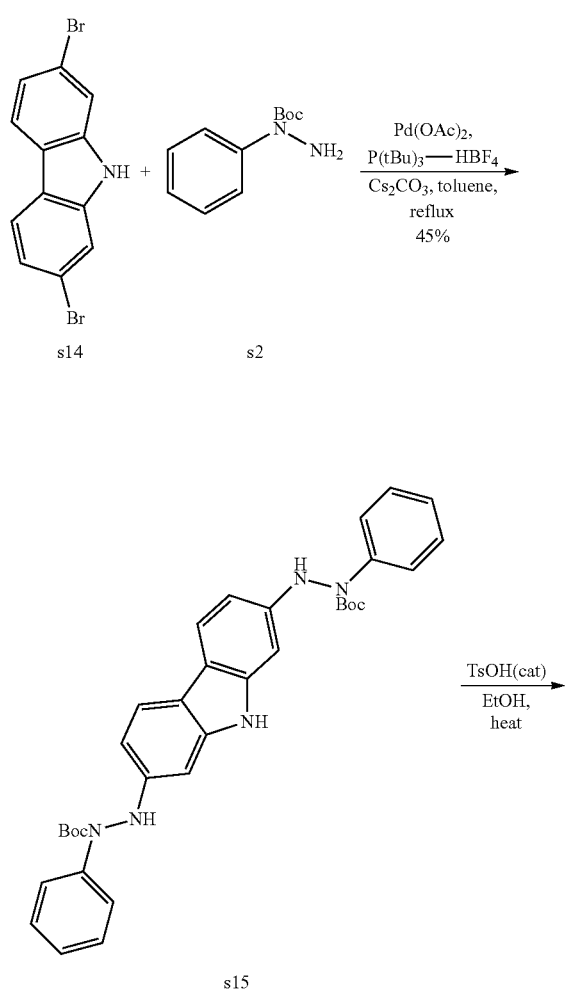

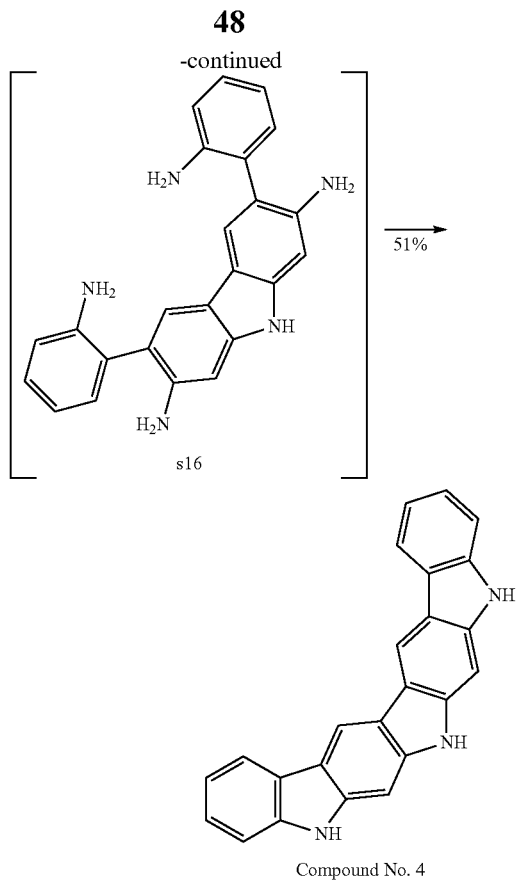

Compound No. 4

Synthesis of reaction intermediate s15: A round bottom flask was filled with a compound s14 (2,7-dibromo-9H-carbazole) of about 268 mg (0.82 mmol), a compound s2 (N-phenyl-hydrazine carboxylic acid tert-butyl ester) of about 206 mg (0.99 mmol), Cs$_2$CO$_3$ of about 376 mg (1.15 mmol), P(t-Bu)$_3$-HBF$_4$ of about 5 mol %, Pd(OAc)$_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s15 of about 214 mg was obtained with a yield of about 45%. $^1$HNMR (400 MHz, CDCl$_3$) δ 11.22 (bs, 1H), 8.22-8.18 (m, 2H), 7.56-7.45 (m, 4H), 7.17 (m, 2H), 6.78-6.74 (m, 2H), 6.67-6.63 (m, 4H), 6.43-6.36 (m, 4H), 1.38 (s, 18H).

Synthesis of compound No. 4: A few drops of conc. HCl were added to a solution in which the compound s15 (diaryl hydrazide) of about 208 mg (0.36 mmol) was dissolved in EtOH of about 10 mL at room temperature. The reaction mixture was heated under reflux for about 8 hours, cooled down to room temperature and neutralized by adding NaHCO$_3$ and then diluted by adding water. A resultant solution was extracted by using CH$_2$Cl$_2$ of about 30 mL several times. A combined solution of the extracted solutions was dried by using MgSO$_4$, concentrated and purified and isolated by column chromatography. As a result, a target compound No. 4 of about 65 mg in accordance with the present invention was obtained with a yield of about 51%. $^1$HNMR (400 MHz, CDCl$_3$) δ 11.25-11.22 (m, 3H), 8.18-8.12 (m, 2H), 7.55-7.42 (m, 8H), 7.22-7.18 (m, 2H).

The synthesis of the compound s14 (2,7-dibromo-9H-carbazole) can be carried out by reference to Freeman, A. W.; Urvoy, M.; Criswell, M. E. *J. Org. Chem.* 2005, 70, 5014.

Example 5

Synthesis of Compound No. 5

A compound No. 5 in accordance with the present invention was synthesized according to a reaction path of the following reaction formula 5:

[Reaction formula 5]

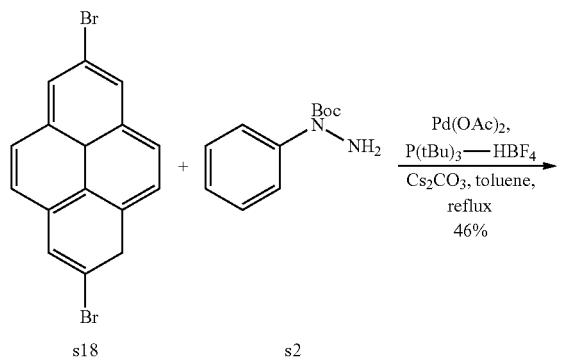

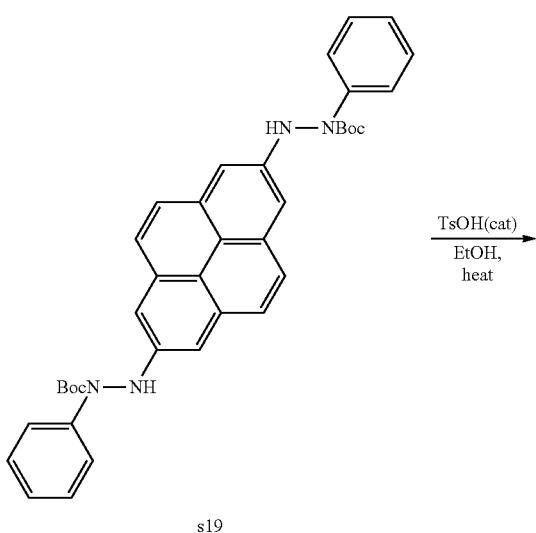

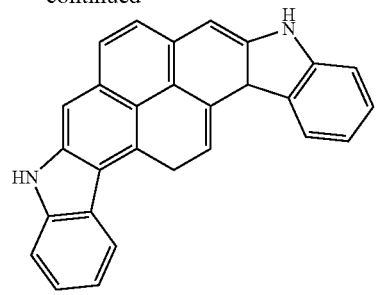

Compound No. 5

Synthesis of reaction intermediate s19: A round bottom flask was filled with a compound s18 (2,7-dibromopyrene) of about 430 mg (1.19 mmol), a compound s2 (N-phenyl-hydrazine carboxylic acid tert-butyl ester) of about 300 mg (1.44 mmol), $Cs_2CO_3$ of about 547 mg (1.68 mmol), $P(t-Bu)_3$-$HBF_4$ of about 5 mol %, $Pd(OAc)_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s19 of about 337 mg was obtained with a yield of about 46%. $^1$HNMR (400 MHz, $CDCl_3$) δ 7.72-7.70 (m, 2H), 7.53-7.48 (m, 6H), 7.42-7.38 (m, 4H), 7.30-7.02 (m, 2H), 6.68-6.64 (m, 2H), 1.38 (s, 18H).

Synthesis of compound No. 5: A few drops of conc. HCl were added to a solution in which the compound s19 (diaryl hydrazide) of about 248 mg (0.40 mmol) was dissolved in EtOH of about 10 mL at room temperature. The reaction mixture was heated under reflux for about 8 hours, cooled down to room temperature and neutralized by adding $NaHCO_3$ and then diluted by adding water. A resultant solution was extracted by using $CH_2Cl_2$ of about 40 mL several times. A combined solution of the extracted solutions was dried by using $MgSO_4$, concentrated and purified and isolated by column chromatography. As a result, a target compound No. 5 of about 80 mg in accordance with the present invention was obtained with a yield of about 52%. $^1$HNMR (400 MHz, $CDCl_3$) δ 11.53 (bs, 2H), 8.22-8.18 (m, 2H), 7.90-7.72 (m, 6H), 7.52-7.22 (m, 6H).

The synthesis of the compound s18 (2,7-dibromopyrene) can be carried out by reference to Lee, H.; Harvey, R. G. *J. Org. Chem.* 1986, 51, 2847.

Example 6

Synthesis of Compound No. 6

A compound No. 6 in accordance with the present invention was synthesized according to a reaction path of the following reaction formula 6:

[Reaction formula 6]

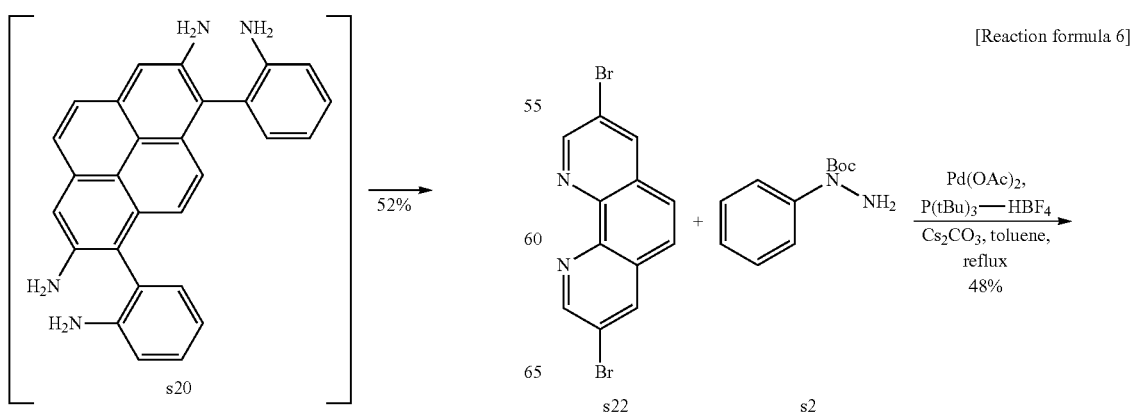

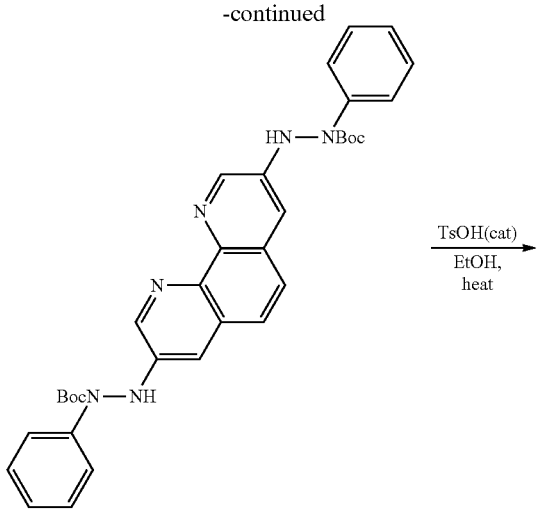

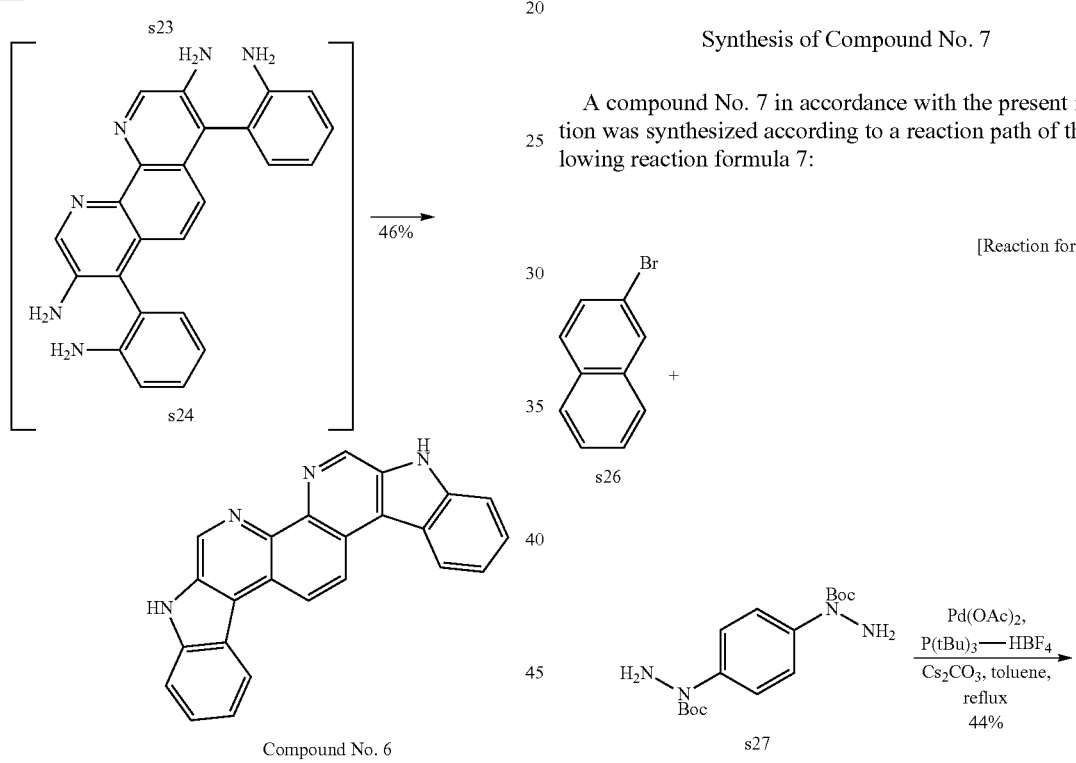

Compound No. 6

Synthesis of reaction intermediate s23: A round bottom flask was filled with a compound s22 (3,8-dibromo-1,10-phenanthroline) of about 322 mg (0.95 mmol), a compound s2 (N-phenyl-hydrazine carboxylic acid tert-butyl ester) of about 236 mg (1.15 mmol), $Cs_2CO_3$ of about 436 mg (1.34 mmol), $P(t-Bu)_3$-$HBF_4$ of about 5 mol %, $Pd(OAc)_2$ of about 5 mol % and toluene anhydride of about 5 mL at room temperature. The reaction mixture was stirred for about 30 minutes and refluxed overnight. The reaction mixture obtained after the reaction was purified and isolated by column chromatography and the intermediate compound s23 of about 366 mg was obtained with a yield of about 65%. $^1$HNMR (400 MHz, $CDCl_3$) δ 8.23 (s, 2H), 7.52-7.38 (m, 6H), 7.12-7.05 (m, 4H), 6.67-6.65 (m, 4H), 1.38 (s, 18H).

Synthesis of compound No. 6: A few drops of conc. HCl were added to a solution in which the obtained intermediate compound s23 (diaryl hydrazide) of about 218 mg (0.37 mmol) was dissolved in EtOH of about 8 mL at room temperature. The reaction mixture was heated under reflux for about 8 hours, cooled down to room temperature and neutralized by adding $NaHCO_3$ and then diluted by adding water. A resultant solution was extracted by using $CH_2Cl_2$ of about 30 mL several times. A combined solution of the extracted solutions was dried by using $MgSO_4$, concentrated and purified and isolated by column chromatography. As a result, a target compound No. 6 of about 50 mg in accordance with the present invention was obtained with a yield of about 38%. $^1$HNMR (400 MHz, $CDCl_3$) δ 11.52 (bs, 2H), 8.82 (s, 2H), 8.20-8.18 (m, 2H), 7.58-7.38 (m, 6H), 7.22-7.18 (m, 2H).

The synthesis of the compound s22 (3,8-dibromo-1,10-phenanthroline) can be carried out by reference to Ciszek, J. W.; Tour, J. M., *Tetrahedron Lett.* 2004, 45, 2801.

Example 7

Synthesis of Compound No. 7

A compound No. 7 in accordance with the present invention was synthesized according to a reaction path of the following reaction formula 7:

[Reaction formula 7]

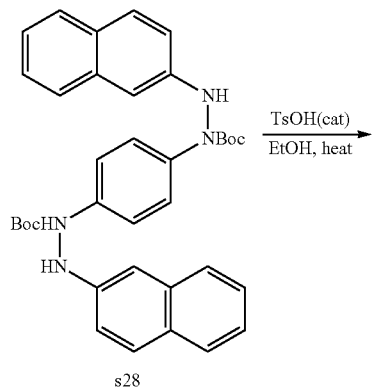

-continued

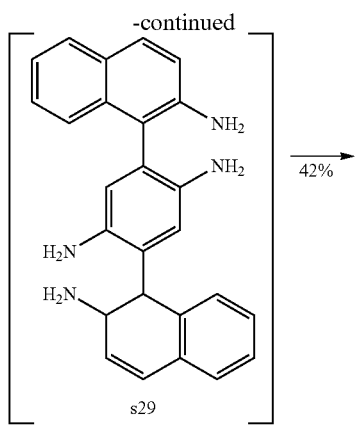

s29

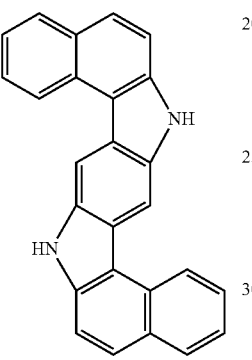

Compound No. 7

Synthesis of reaction intermediate s28: A round bottom flask was filled with a compound s26 (2-dibromonaphtalene) of about 439 mg (2.12 mmol), a compound s27, (di-tert-butyl 1,1'-(1,4-phenylene)bis(hydrazine carboxylate)) of about 344 mg (1.01 mmol), $Cs_2CO_3$ of about 800 mg (2.44 mmol), $P(t-Bu)_3$-$HBF_4$ of about 5 mol %, $Pd(OAc)_2$ of about 5 mol % and toluene anhydride of about 15 mL at room temperature. The reaction mixture was stirred for about 30 minutes and refluxed overnight. The reaction mixture obtained after the reaction was purified and isolated by column chromatography and the intermediate compound s28 of about 264 mg was obtained with a yield of about 44%. $^1$HNMR (400 MHz, $CDCl_3$) δ 7.92-7.88 (m, 4H), 7.64-7.35 (m, 8H), 6.82-6.58 (m, 6H), 1.39 (s, 18H).

Synthesis of compound No. 7: A few drops of conc. HCl were added to a solution in which the obtained intermediate compound s28 (diaryl hydrazide) of about 202 mg (0.34 mmol) was dissolved in EtOH of about 8 mL at room temperature. The reaction mixture was heated under reflux for about 8 hours, cooled down to room temperature and neutralized by adding $NaHCO_3$ and then diluted by adding water. A resultant solution was extracted by using $CH_2Cl_2$ of about 30 mL several times. A combined solution of the extracted solutions was dried by using $MgSO_4$, concentrated and purified and isolated by column chromatography. As a result, a target compound No. 7 of about 51 mg in accordance with the present invention was obtained with a yield of about 42%. $^1$HNMR (400 MHz, $CDCl_3$) δ 11.52 (bs, 2H), 8.56-8.52 (m, 2H), 7.98-7.96 (m, 2H), 7.72-7.42 (m, 8H), 7.10-7.08 (m, 2H).

Example 8

As can be seen from the following reaction formula and Table 1 showing a result of synthesis, a novel substituent instead of Boc was added to nitrogen of the polycyclic aromatic organic semiconductor compound in accordance with the present invention. When a functional group of carbobenzyloxy (Cbz) was used, transformation yields described below were obtained from a methanol solvent with a catalyst of sulfuric acid:

TABLE 1

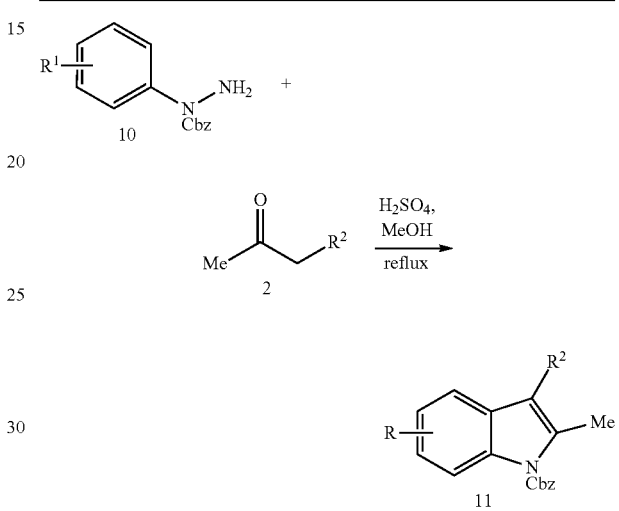

| entry | 10 | 2 | time | N-CBz-indole |
|---|---|---|---|---|
| 1 | 10a ($R^1$ = H) | 2a ($R^2$ = Me) | 2 h | 11a (95%) |
| 2 | 10b ($R^1$ = p-OMe) | 2a ($R^2$ = Me) | 2 h | 11b (91%) |
| 3 | 10c ($R^1$ = p-Me) | 2a ($R^2$ = Me) | 2 h | 11c (84%) |
| 4 | 10d ($R^1$ = p-$CO_2$Me) | 2a ($R^2$ = Me) | 72 h | 11d (50%) |
| 5 | 10a ($R^1$ = H) | 2b ($R^2$ = nBu) | 4 h | 11e (71%) |
| 6 | 10b ($R^1$ = p-OMe) | 2c ($R^2$ = $CH_2CO_2Me$) | 24 h | 11f (73%) |
| 7 | 10e ($R^1$ = p-tBu) | 2a ($R^2$ = Me) | 4 h | 11g (77%) |
| 8 | 10f ($R^1$ = p-Ph) | 2a ($R^2$ = Me) | 8 h | 11h (93%) |
| 9 | 10g ($R^1$ = p-Br) | 2a ($R^2$ = Me) | 12 h | 11i (75%) |
| 10 | 10h ($R^1$ = p-$NH_2$) | 2a ($R^2$ = Me) | 12 h | 11j (77%) |
| 11 | 10i ($R^1$ = o-Me) | 2a ($R^2$ = Me) | 2 h | 11k (40%) |
| 12 | 10j ($R^1$ = m-OMe) | 2a ($R^2$ = Me) | 12 h | 11l (91%)[a] |

[a]6:4 mixture of two regioisomers

Example 9

As can be seen from the following reaction formula and Table 2 showing a result of synthesis, when cyclohexanone reacted with hydrazide having a functional group of Cbz at a position of nitrogen, tetrahydro-N-Cbz was produced and this tetrahydro-N-Cbz reacted with an oxidizer such as 2,3-dichloro-5,6-dicyano-1,4-benzoquinone (DDQ). As a result, N-Cbz-carbazole was produced with a very high yield:

TABLE 2

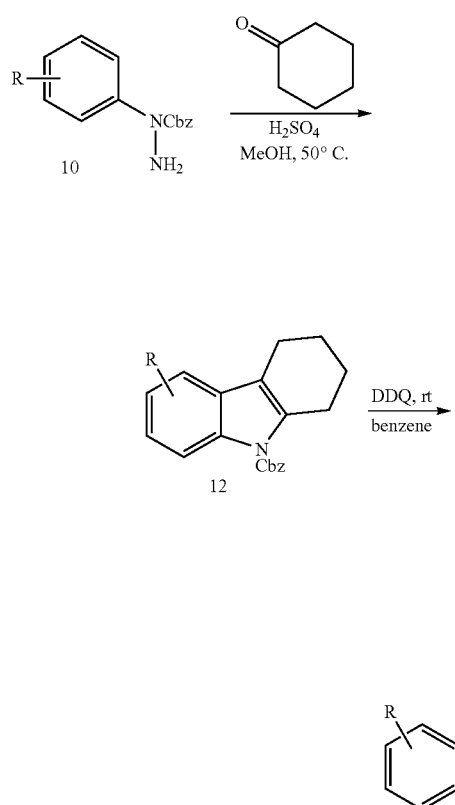

| entry | arylhydrazide | time | 12 (yield) | time | 13 (yield) |
|---|---|---|---|---|---|
| 1 | 10a ($R^1$ = H) | 2 h | 12a (86%) | 1 h | 13a (87%) |
| 2 | 10b ($R^1$ = p-OMe) | 2 h | 12b (98%) | 1 h | 13b (85%) |
| 3 | 10c ($R^1$ = p-Me) | 2 h | 12c (98%) | 1 h | 13c (80%) |
| 4 | 10d ($R^1$ = p-$CO_2$Me) | 5 h | 12d (70%) | 3 h[a] | 13d (49%) |
| 5 | 10e ($R^1$ = p-t-Bu) | 6 h | 12e (85%) | 1 h | 13e (86%) |
| 6 | 10f ($R^1$ = p-Ph) | 6 h | 12f (86%) | 1 h | 13f (86%) |
| 7 | 10j ($R^1$ = m-OMe) | 6 h | 12j (53%)[b] | 1 h | 13j (80%) |
|   |   |   | 12j' (32%)[b] | 1 h | 13j' (88%) |
| 8 | 10k ($R^1$ = m-Me) | 3 h | 12k (87%)[c] | 1 h | 13k (67%)[c] |
| 9 | 10l ($R^1$ = p-hexyl) | 6 h | 12l (87%) | 1 h | 13l (77%) |

[a]at 50° C.;
[b]two regioisomers 12j (R = 6-OMe) and 12j'(R = 4-OMe) were separated and subjected to aromatization;
[c]for a mixture of two regioisomers.

Example 10

As can be seen from the following reaction formula and Table 3 showing a result of synthesis, when 1,4-diiodobenzene reacted with benzyl carbazate in the presence of a catalyst of Cu(I), bis-hydrazide was produced and this bis-hydrazide reacted with keton. As a result, pyrro[2,3-f]indole and pyrro[3,3-e]indole were synthesized economically with a high yield:

TABLE 3

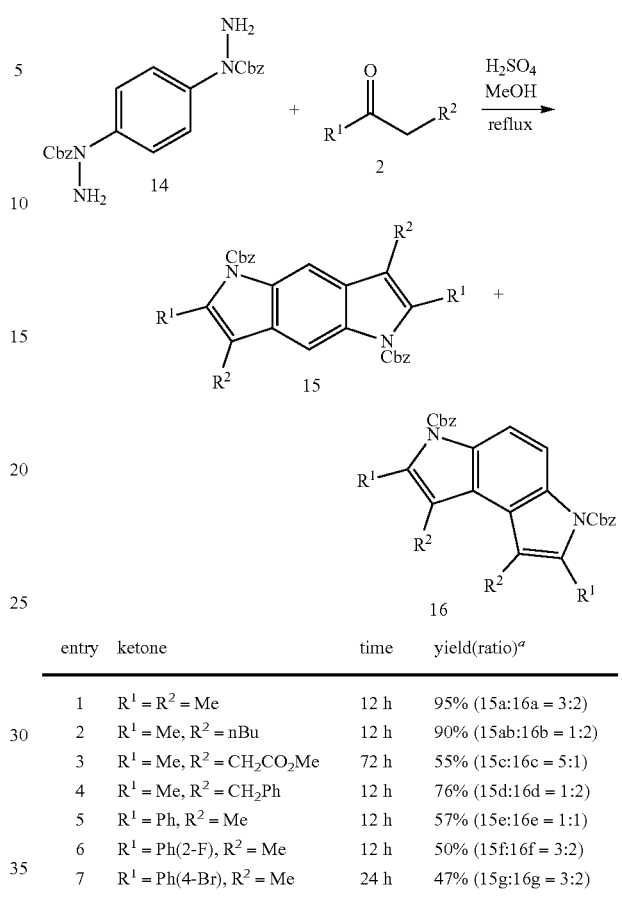

| entry | ketone | time | yield(ratio)[a] |
|---|---|---|---|
| 1 | $R^1$ = $R^2$ = Me | 12 h | 95% (15a:16a = 3:2) |
| 2 | $R^1$ = Me, $R^2$ = nBu | 12 h | 90% (15ab:16b = 1:2) |
| 3 | $R^1$ = Me, $R^2$ = $CH_2CO_2$Me | 72 h | 55% (15c:16c = 5:1) |
| 4 | $R^1$ = Me, $R^2$ = $CH_2$Ph | 12 h | 76% (15d:16d = 1:2) |
| 5 | $R^1$ = Ph, $R^2$ = Me | 12 h | 57% (15e:16e = 1:1) |
| 6 | $R^1$ = Ph(2-F), $R^2$ = Me | 12 h | 50% (15f:16f = 3:2) |
| 7 | $R^1$ = Ph(4-Br), $R^2$ = Me | 24 h | 47% (15g:16g = 3:2) |

[a]total isolated yield (ratio determined by $^1$H NMR)

Example 11

Manufacturing Solar Cell Using Organic Semiconductor Compound in Accordance with Present Invention After titanium dioxide (TiO2) powder of about 1 g was mixed with water of about 5 mL and isopropane alcohol of about 5 mL, acetyl acetone of about 70 μg and some surfactant and polyethylene glycol were added thereto. The mixture was ground well in a mortar for about 20 minutes and then coated on a transparent conductive substrate to a thickness of about 10 μm. The titanium dioxide thin film was sintered at about 450° C. for about 30 minutes and then cooled down to room temperature. The organic semiconductor compound No. 1 synthesized in the example 1 was dissolved in a solvent of chloroform and then coated on the titanium dioxide thin film by using a spin coater. Aluminum as a counter electrode was vapor-deposited on a thin film of the compound No. 1 coated on the titanium dioxide thin film to manufacture a solar cell. A light of AM 1.5 and 100 mW/cm$^2$ was irradiated to the manufactured solar cell and as a result, a light conversion efficiency of about 2.51% was measured.

Example 12

Manufacturing Solar Cell Using Organic Semiconductor Compound in Accordance with Present Invention Poly(3,4-ethylenedioxythiophene)-poly(styrene-sulfonate) (PEDOT:PSS) was coated on a transparent conductive electrode by using a spin coater to form a thin film and then sintered at about 120° C. for about 20 minutes. The organic semiconductor compound No. 2 synthesized in the example 2 was dissolved in a solvent of chloroform and then coated on titanium dioxide by using a spin coater. Gold as a counter electrode was vapor-deposited on a thin film of the compound No. 2 to manufacture a solar cell. A light of AM 1.5 and 100 mW/cm$^2$ was irradiated to the manufactured solar cell and as a result, a light conversion efficiency of about 4.02% was measured.

Example 13

Manufacturing Solar Cell Using Organic Semiconductor Compound in Accordance with Present Invention After zinc oxide nano powder of about 1 g was mixed with water of about 5 mL and isopropane alcohol of about 5 mL, acetyl acetone of about 70 μg and some surfactant and polyethylene glycol were added thereto. The mixture was ground well in a mortar for about 20 minutes and then coated on a transparent conductive substrate to a thickness of about 10 μm. The zinc oxide thin film was sintered at about 250° C. for about 30 minutes and then cooled down to room temperature. The organic semiconductor compound No. 5 synthesized in the example 5 was dissolved in a solvent of chloroform and then coated on the zinc oxide thin film by using a spin coater. Aluminum as a counter electrode was vapor-deposited on a thin film of the compound No. 5 to manufacture a solar cell. A light of AM 1.5 and 100 mW/cm$^2$ was irradiated to the manufactured solar cell and as a result, a light conversion efficiency of about 5.43% was measured.

Although the present invention has been explained in detail in the above-described examples, the present invention is not limited thereto and can be changed and modified in various ways. It is clear that various modifications can be made in a scope of the present invention by those skilled in the art.

INDUSTRIAL APPLICABILITY

A novel polycyclic aromatic organic semiconductor compound having a polycyclic aromatic core in accordance with the present invention can be used in an electronic, optical or electro-optical device such as an organic semiconductor composition, organic semiconductor thin film, organic field effect transistor and solar cell containing the compound, and the electronic, optical or electro-optical device can be applied to a device selected from the group including a thin film transistor (TFT), an integrated circuit (IC) component, a radio frequency identification (RFID) tag, an electronic light emitting display, a flat panel display, a backlight, a photodetector, a logic circuit, a memory device, a capacitor, a charge injecting layer, a Schottky diode, a planarising layer, an antistatic film, a conductive substrate or pattern, a photoconductor and an electrophotographic device.

What is claimed is:

1. A polycyclic aromatic organic semiconductor compound selected from the group consisting of the following formulas:

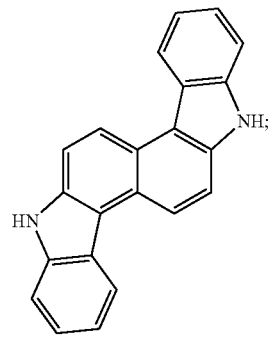

Compound No. 1

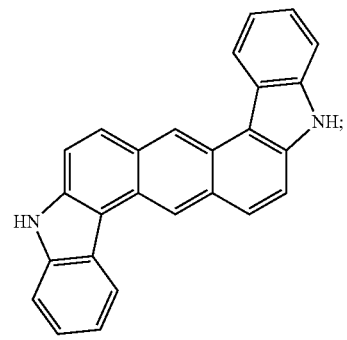

Compound No. 2

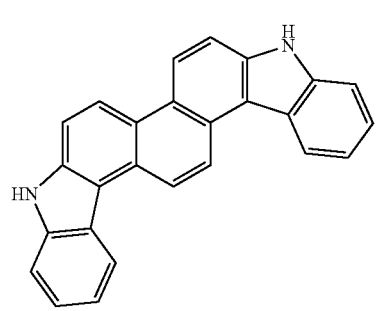

Compound No. 3

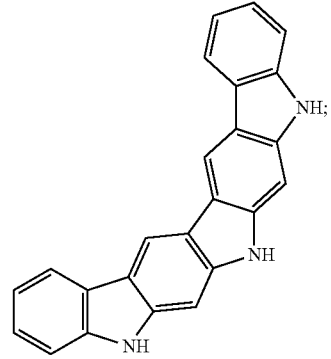

Compound No. 4

Compound No. 5
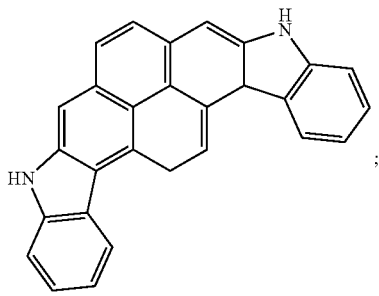
;

Compound No. 6
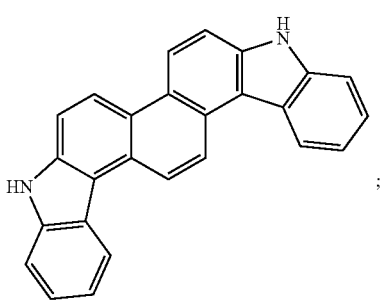
and,

Compound No. 7
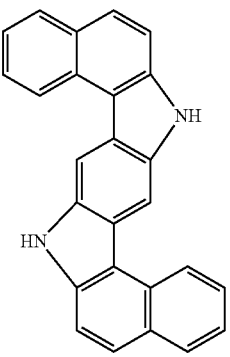

2. An organic semiconductor composition, comprising one or more polycyclic aromatic organic semiconductor compounds claimed in claim 1 which are dissolved or dispersed in a solvent.

3. An organic semiconductor thin film, comprising one or more polycyclic aromatic organic semiconductor compounds claimed in claim 1.

4. An electronic, optical or electro-optical device, comprising one or more polycyclic aromatic organic semiconductor compounds claimed in claim 1.

5. An organic field effect transistor, comprising one or more polycyclic aromatic organic semiconductor compounds claimed in claim 1.

6. An organic light emitting diode, comprising one or more polycyclic aromatic organic semiconductor compounds claimed in claim 1.

7. An organic solar cell, comprising one or more polycyclic aromatic organic semiconductor compounds claimed in claim 1.

8. A sensor, comprising one or more polycyclic aromatic organic semiconductor compounds claimed in claim 1.

9. The electronic, optical or electro-optical device of claim 4, which is selected from the group consisting of a thin film transistor (TFT), an integrated circuit component, a radio frequency identification (RFID) tag, an electronic light emitting display, a flat panel display, a backlight, a photodetector, a logic circuit, a memory device, a capacitor, a charge injecting layer, a Schottky diode, a planarising layer, an antistatic film, a conductive substrate or pattern, a photoconductor and an electrophotographic device.

10. An electronic, optical or electro-optical device, comprising an organic semiconductor thin film claimed in claim 3.

11. An organic field effect transistor, comprising an organic semiconductor thin film claimed in claim 3.

12. An organic light emitting diode, comprising an organic semiconductor thin film claimed in claim 3.

13. An organic solar cell, comprising an organic semiconductor thin film claimed in claim 3.

14. A sensor, comprising an organic semiconductor thin film claimed in claim 3.

* * * * *